United States Patent
Noshi et al.

(10) Patent No.: US 9,433,388 B2
(45) Date of Patent: Sep. 6, 2016

(54) IMAGE DIAGNOSIS APPARATUS AND METHOD

(71) Applicants: Kabushiki Kaisha Toshiba, Minato-ku (JP); Toshiba Medical Systems Corporation, Otawara (JP)

(72) Inventors: Yasuhiro Noshi, Otawara (JP); Manabu Teshigawara, Otawara (JP); Satoru Nakanishi, Utsunomiya (JP); Takuzo Takayama, Utsunomiya (JP)

(73) Assignee: Toshiba Medical Systems Corpoeration, Otawara-shi (JP)

( * ) Notice: Subject to any disclaimer, the term of this patent is extended or adjusted under 35 U.S.C. 154(b) by 112 days.

(21) Appl. No.: 13/891,786

(22) Filed: May 10, 2013

(65) Prior Publication Data
US 2013/0251102 A1   Sep. 26, 2013

Related U.S. Application Data

(63) Continuation of application No. PCT/JP2011/076211, filed on Nov. 14, 2011.

(30) Foreign Application Priority Data

Nov. 12, 2010   (JP) .................. 2010-253982

(51) Int. Cl.
*A61B 6/03* (2006.01)
*A61B 6/04* (2006.01)
(Continued)

(52) U.S. Cl.
CPC ............. *A61B 6/0407* (2013.01); *A61B 6/032* (2013.01); *A61B 6/037* (2013.01); *A61B 6/0457* (2013.01);
(Continued)

(58) Field of Classification Search
CPC .... A61B 6/032; A61B 6/037; A61B 6/0457; A61B 6/12; A61B 6/4417
USPC ................................. 378/4–20, 63
See application file for complete search history.

(56) References Cited

U.S. PATENT DOCUMENTS 6,895,105 B2 * 5/2005 Wollenweber ............... 382/131
7,020,315 B2 * 3/2006 Vaisburd et al. ............. 382/131
(Continued)

FOREIGN PATENT DOCUMENTS

JP   2002-330960   11/2002
JP   2005-291814   10/2005
(Continued)

OTHER PUBLICATIONS

International Search Report mailed Dec. 20, 2011, in PCT/JP2011/076211 filed Nov. 14, 2011 (with English Translation).
(Continued)

Primary Examiner — Hoon Song
(74) Attorney, Agent, or Firm — Oblon, McClelland, Maier & Neustadt, L.L.P.

(57) ABSTRACT

According to the present embodiment, an image diagnosis apparatus includes a first image taking device that takes an image of a patient placed on a couchtop by using an X-ray emission; a second image taking device that takes images in positions by moving an image taking position of the patient by a predetermined distance at a time, along the body-axis direction; a position estimating unit; and a correction processing unit. The position estimating unit estimates a couchtop position for each of the image taking positions of the second image taking device, based on information about warping of the couchtop of the first image taking device. The correction processing unit uses information about the couchtop positions estimated by the position estimating unit, for performing a position correcting process on the images obtained by the image taking devices.

14 Claims, 24 Drawing Sheets

(51) Int. Cl.
    *A61B 6/00*    (2006.01)
    *G01T 1/161*   (2006.01)
(52) U.S. Cl.
    CPC .......... *A61B 6/4258* (2013.01); *A61B 6/4417* (2013.01); *A61B 6/5264* (2013.01); *G01T 1/1611* (2013.01); *A61B 6/5247* (2013.01)

(56) References Cited

U.S. PATENT DOCUMENTS

| 2002/0081008 | A1 | 6/2002 | Wollenweber |
| 2006/0184012 | A1 | 8/2006 | Marzendorfer |
| 2008/0123924 | A1 | 5/2008 | Nabatame et al. |

FOREIGN PATENT DOCUMENTS

| JP | 2006-175236 | 7/2006 |
| JP | 2007-7415 A | 1/2007 |
| JP | 2008-29828 | 2/2008 |
| JP | 2008-183142 | 8/2008 |
| JP | 2010-99396 | 5/2010 |

OTHER PUBLICATIONS

International Written Opinion mailed Dec. 20, 2011, in PCT/JP2011/076211 filed Nov. 14, 2011.
Japanese Office Action issued Jan. 12, 2016 in Patent Application No. 2011-249099 (without English Translation).

* cited by examiner

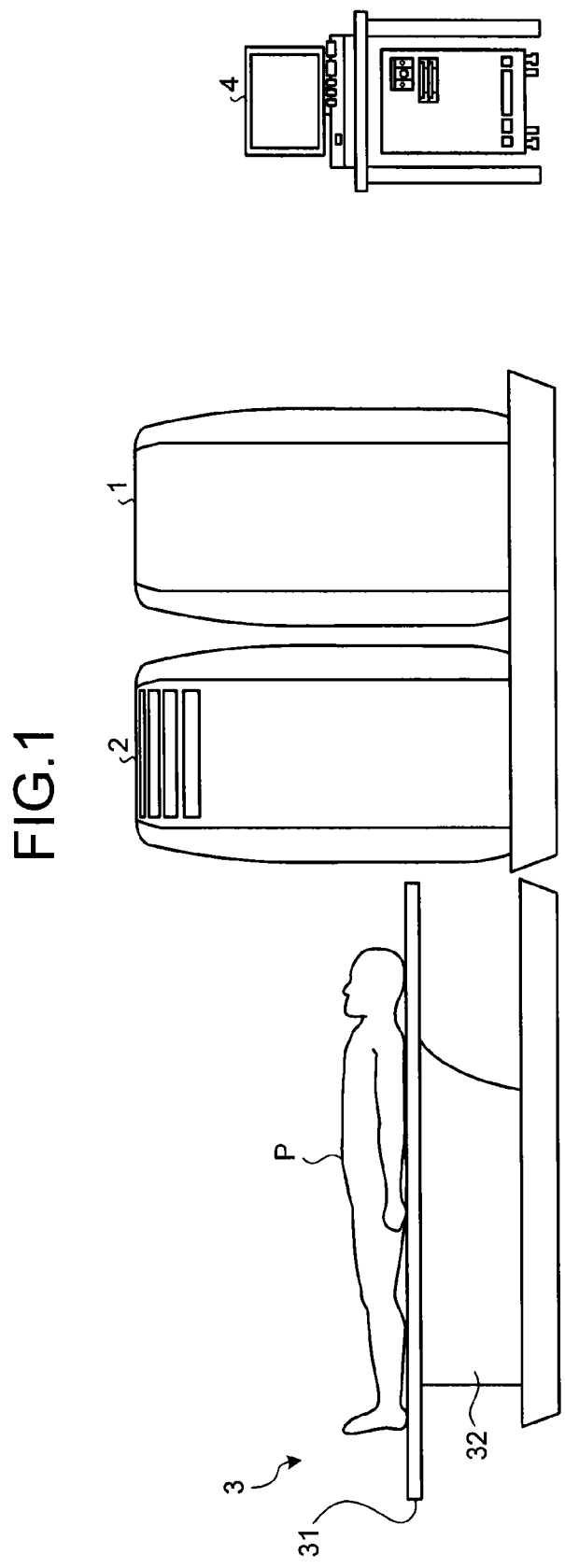

FIG.12
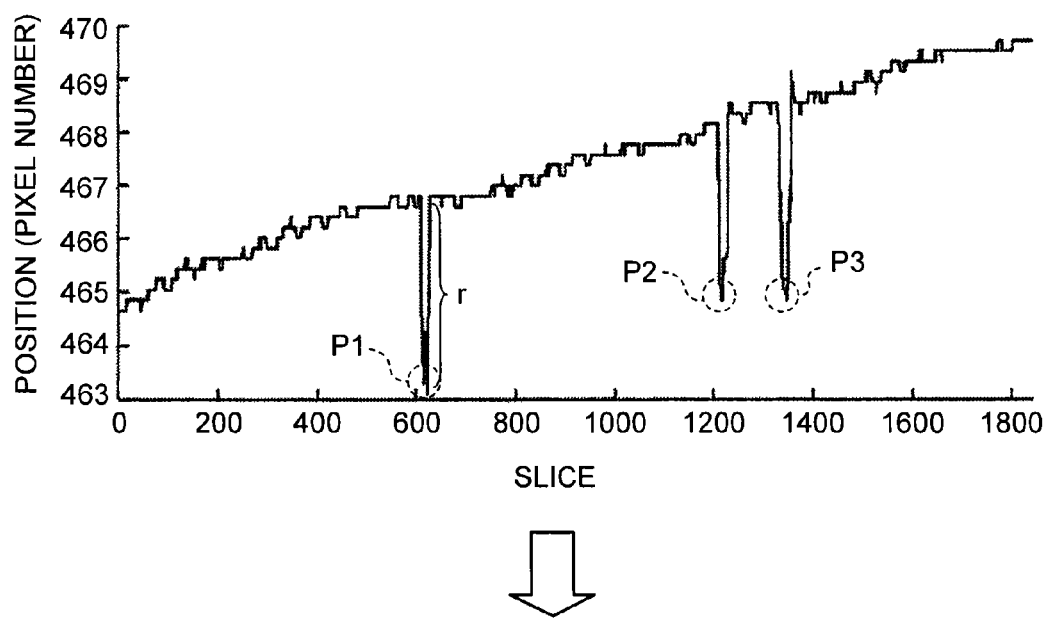
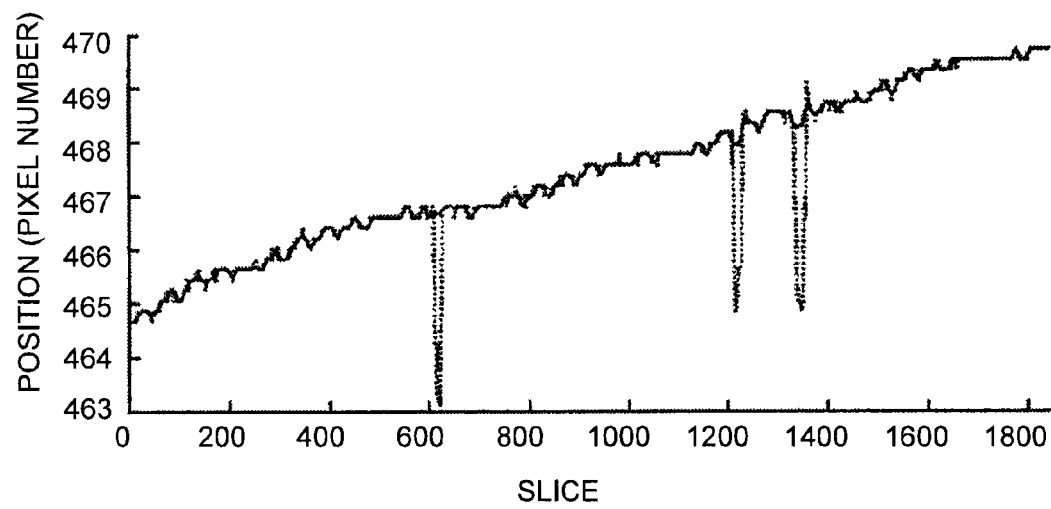

FIG.14
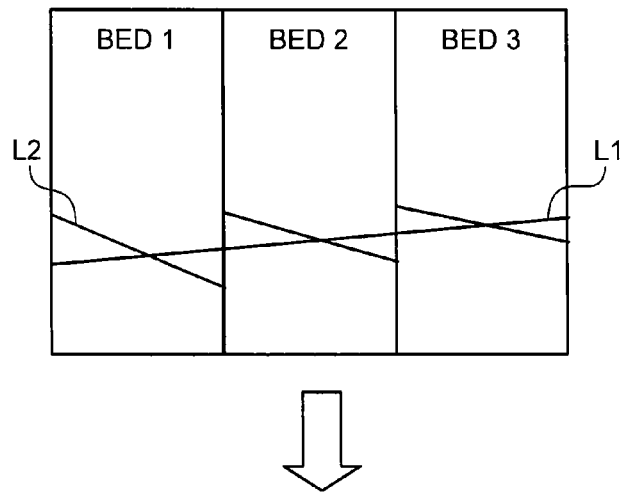
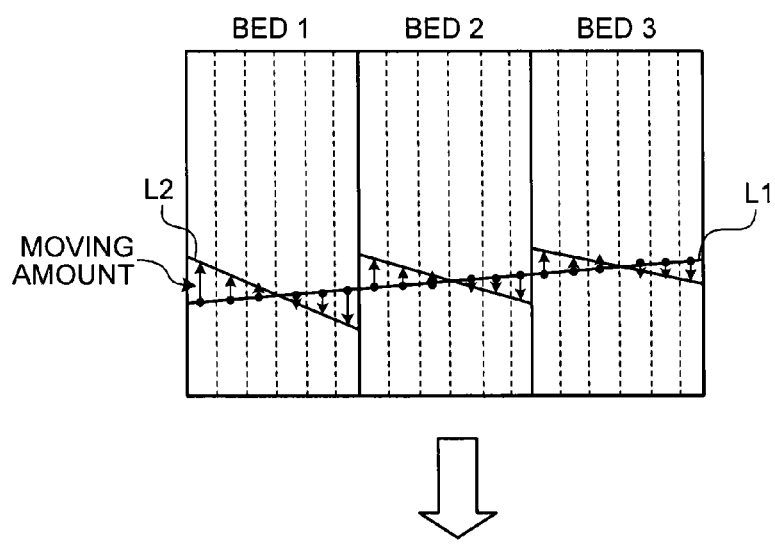
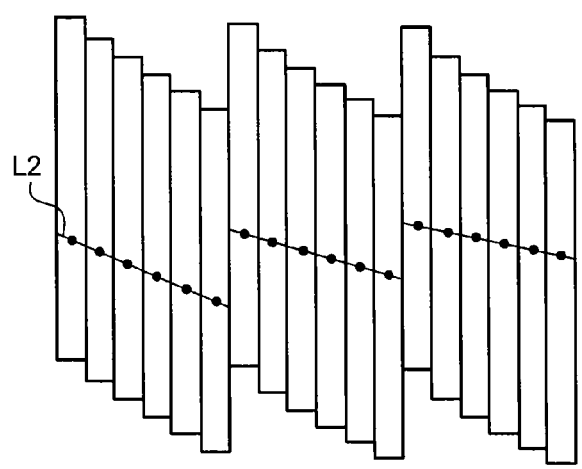

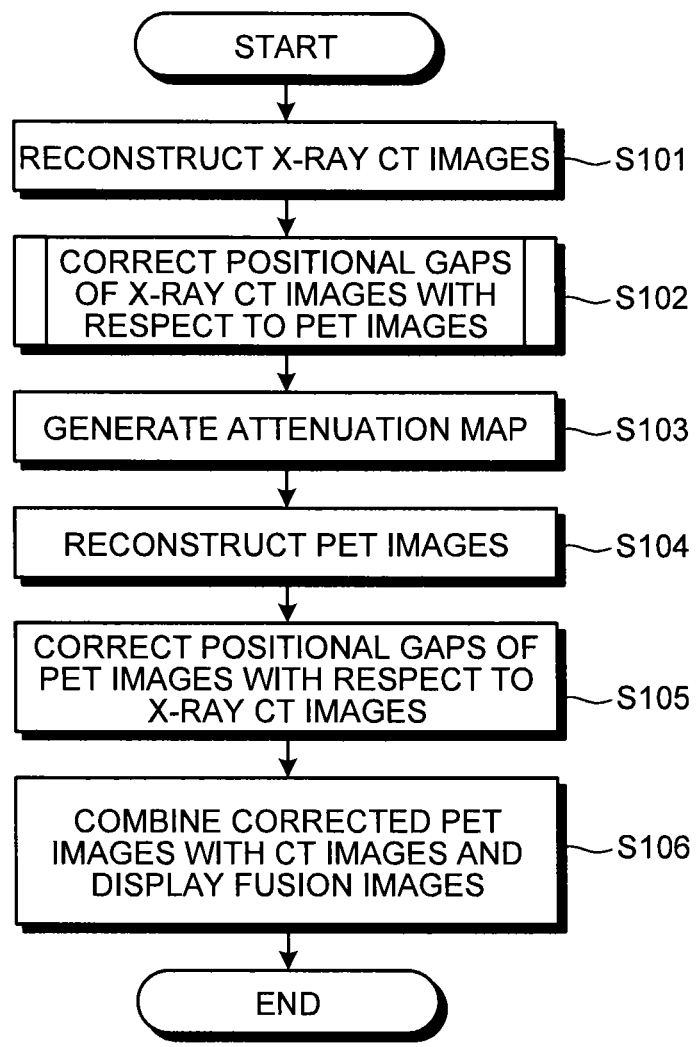

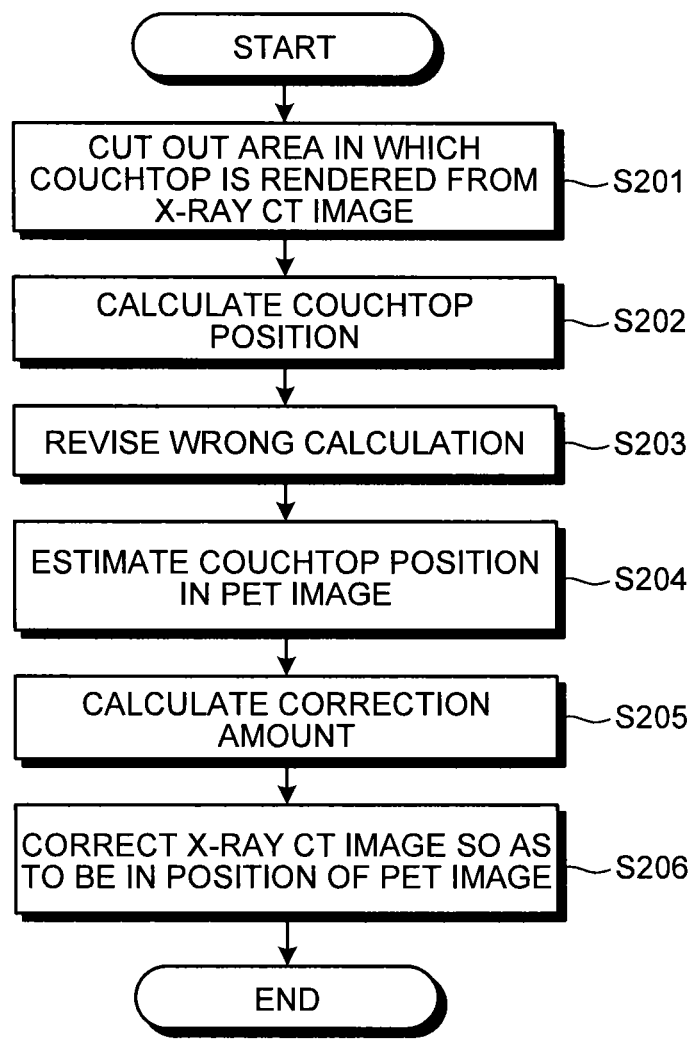

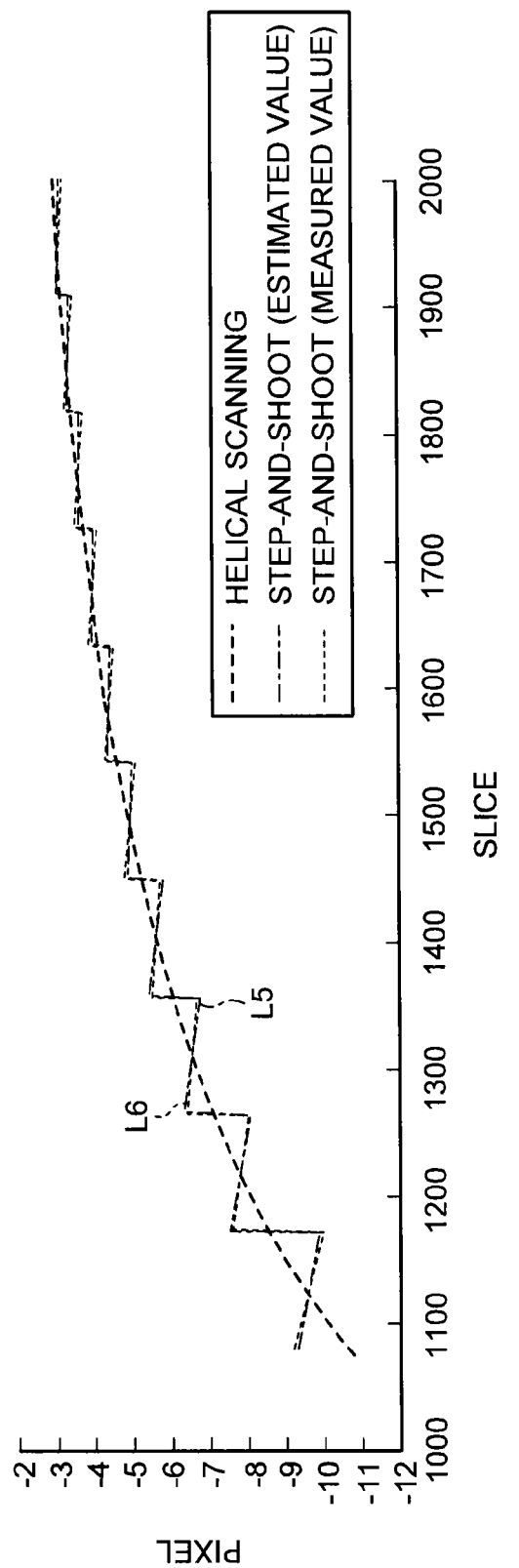

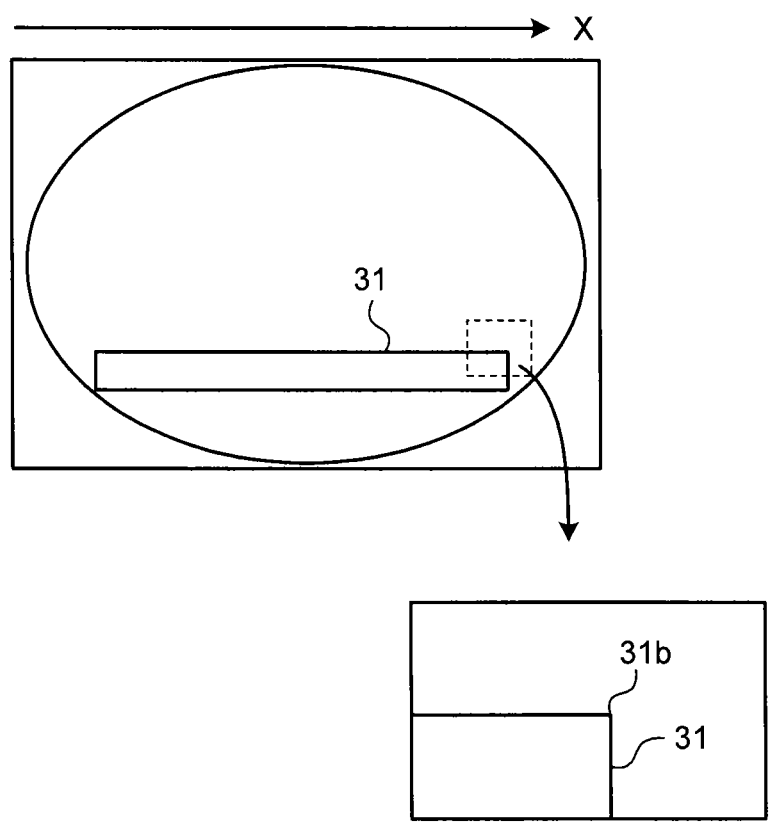

111
IMAGE DIAGNOSIS APPARATUS AND METHOD

CROSS-REFERENCE TO RELATED APPLICATIONS

This application is a continuation of PCT international application Ser. No. PCT/JP2011/076211 filed on Nov. 14, 2011 which designates the United States, and which claims the benefit of priority from Japanese Patent Application No. 2010-253982, filed on Nov. 12, 2010; the entire contents of which are incorporated herein by reference.

FIELD

Embodiments described herein relate generally to an image diagnosis apparatus and an image diagnosis method.

BACKGROUND

Conventionally, medical image diagnosis apparatuses capable of imaging the inside of an examined subject (hereinafter, "patient") for whom a diagnosis is to be made are commonly used in the medical field. Examples of medical image diagnosis apparatuses being used include nuclear medical imaging apparatuses such as Single Photon Emission Computed Tomography (SPECT) apparatuses and Positron Emission Computed Tomography (PET) apparatuses, as well as X-ray Computed Tomography (CT) apparatuses, and Magnetic Resonance Imaging (MRI) apparatuses.

Further, in recent years, apparatuses in each of which a plurality of medical image diagnosis apparatuses are integrated together are in practical use. Examples of such an apparatus in practical use include an apparatus (e.g., a PET-CT apparatus or a SPECT-CT apparatus) in which a nuclear medical imaging apparatus capable of making a functional diagnosis of a tissue in the body of a patient is integrated together with an X-ray CT apparatus capable of imaging morphological information of a tissue in the body of a patient.

For example, a medical examination is performed to find out which part of a patient's body is suffering from what kind of disease (e.g., a tumor), by using a PET-CT apparatus that generates a fusion image in which a PET image and an X-ray CT image are superimposed on each other. Further, with regard to radiation treatment planning using X-ray CT images, it is known that it is possible to improve the precision level of the radiation treatment planning when one or more PET images are used in addition to the X-ray CT images.

Incidentally, in those apparatuses described above where a plurality of medical image diagnosis apparatuses are integrated together, mutually-different image taking methods are used, in some situations, to take images with the medical image diagnosis apparatuses. For example, a PET-CT apparatus takes PET images by using a step-and-shoot method by which a couchtop on which a patient is placed is moved in stages along the body-axis direction so as to obtain images of different parts, and also, takes X-ray CT images by using a helical scanning method by which images are taken while moving a couchtop on which the patient is placed along the body-axis direction.

With the conventional technique, however, the precision level of the images is deteriorated in some situations due to a positional gap between the images taken by using the mutually-different image taking methods.

BRIEF DESCRIPTION OF THE DRAWINGS

FIG. 1 is a drawing for explaining an overall configuration of a PET-CT apparatus according to a first embodiment.

FIG. 12 is a drawing that schematically illustrates an exemplary process performed by a position revising unit.

FIG. 14 is a drawing that schematically illustrates an exemplary process performed by a correction processing unit to align positions of X-ray CT images with PET images.

FIG. 16 is a flowchart of an image processing procedure performed by the PET-CT apparatus according to the first embodiment.

FIG. 17 is a flowchart of a correcting process procedure performed on an X-ray CT image by the PET-CT apparatus according to the first embodiment.

FIG. 18B is a chart of a simulation result obtained when a 200-kilogram weight is applied to a couchtop.

FIG. 21 is a drawing that schematically illustrates an exemplary process performed by a position calculating unit according to a second embodiment.

DETAILED DESCRIPTION

In general, according to one embodiment, an image diagnosis apparatus includes a first image taking device, a second image taking device, an estimating unit and a position correcting unit. The first image taking device configured to take an image of a patient placed on a couchtop by using an X-ray emission. The second image taking device configured to take images in positions by moving an image taking position of the patient by a predetermined distance at a time, along a body-axis direction. The estimating unit configured to estimate a couchtop position for each of the image taking positions of the second image taking device, based on information about warping of the couchtop of the first image taking device. The position correcting unit configured to use information about the couchtop positions estimated by the estimating unit for performing a position correcting process on the images obtained by the image taking devices.

Hereinafter, embodiments will be described with reference to the drawings.

First Embodiment

In a first embodiment, an example will be explained where a PET-CT apparatus is used as an apparatus in which medical image diagnosis apparatuses using mutually-different image taking methods are integrated together. First, an overall configuration of a PET-CT apparatus according to the first embodiment will be explained, with reference to FIG. 1. FIG. 1 is a drawing for explaining the overall configuration of the PET-CT apparatus according to the first embodiment. As shown in FIG. 1, the PET-CT apparatus according to the first embodiment includes a PET gantry device 1, a CT gantry device 2, a couch device 3, and a console device 4.

Figure 2A:
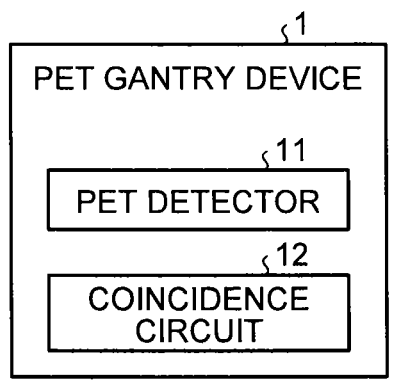
FIG. 2A is a drawing for explaining a configuration of a PET gantry device.

The PET gantry device 1 is a device that generates projection data of gamma rays (hereinafter, "gamma ray projection data") for reconstructing a PET image by detecting a pair of gamma rays emitted from a tissue of a patient's body that has admitted a positron emitting nuclide applied to the patient P. FIG. 2A is a drawing for explaining a configuration of the PET gantry device.

As shown in FIG. 2A, the PET gantry device 1 includes a PET detector 11 and a coincidence circuit 12. The PET detector 11 is a detector that uses a photon counting method by which the gamma rays emitted from the patient P are detected. More specifically, the PET detector 11 is configured by disposing a plurality of PET detector modules 111 so as to surround the patient P in the form of a ring.

Figure 2B:
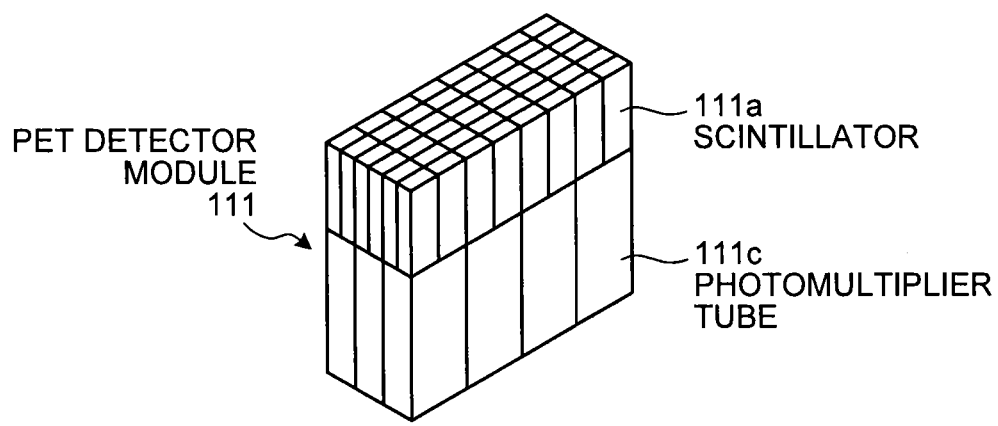
FIG. 2B is a drawing for explaining a configuration of a PET detector.

FIG. 2B is a drawing for explaining a configuration of the PET detector. For example, as shown in FIG. 2B, each of the PET detector modules 111 is configured with an Anger detector including scintillators 111a and Photomultiplier Tubes (PMT) 111c.

In the scintillators 111a, as shown in FIG. 2B, a plurality of pieces of NaI or BGO, which are capable of converting the gamma rays that are emitted from the patient P and entered therein into visible light, are arranged in a two-dimensional formation. Further, the photomultiplier tubes 111c are devices that multiply and convert the visible light output from the scintillators 111a into electric signals. The plurality of photomultiplier tubes are densely arranged as shown in FIG. 2B.

Each of the photomultiplier tubes 111c is configured with a photocathode that receives scintillation light and generates photoelectrons; multiple stages of dynodes that create electric fields for accelerating the generated photoelectrons; and an anode from which electrons flow out. The electrons emitted from the photocathode due to the photoelectric effect are accelerated toward a dynode and collide with the surface of the dynode, so as to knock out additional electrons. When this phenomenon is repeated at the multiple stages of dynodes, the number of electrons is multiplied in the manner of an avalanche so that the number of electrons reaches as many as approximately 1 million at the anode. In this example, the gain factor of the photomultiplier tube 111c is 1 million times. To cause this multiplication utilizing the avalanche phenomenon, a voltage of 1000 volts or higher is usually applied to between the dynodes and the anode.

In this manner, each of the PET detector modules 111 counts the number of gamma rays emitted from the patient P, by converting the gamma rays into the visible light by using the scintillators 111a and further converting the converted visible light into the electric signals by using the photomultiplier tubes 111c.

Further, the coincidence circuit 12 shown in FIG. 2A is connected to each of the plurality of photomultiplier tubes 111c included in each of the plurality of PET detector modules 111. Further, the coincidence circuit 12 generates a coincidence list for determining entering directions of the pair of gamma rays emitted from the positrons, based on output results of the PET detector modules 111. More specifically, the coincidence circuit 12 determines the entering positions of the gamma rays (the positions of the scintillators 111a) by calculating the positions of such photomultiplier tubes 111c that converted the visible light output from the scintillators 111a into the electric signals and that output the electric signals at the same time and by calculating the position of the gravity point based on the strengths of the electric signals. Further, the coincidence circuit 12 calculates energy values of the entering gamma rays by performing a calculation process (integral processing and differential processing) on the strengths of the electric signals output by the photomultiplier tubes 111c.

Further, the coincidence circuit 12 performs a coincidence finding process to obtain, out of the output results of the PET detector 11, a set of pieces of data of which the gamma ray entering times are within a predetermined time window range and of which the energy values are both within a predetermined energy window range. For example, a time window range of 2 nanoseconds and an energy window range of 350 keV to 550 keV are set as search conditions. Further, the coincidence circuit 12 generates the coincidence list by using an output result having the set of pieces of data found in the search as information indicating coincidence of two annihilation photons. Further, the coincidence circuit 12 transmits the coincidence list to the console device 4 shown in FIG. 1, as the gamma ray projection data for reconstructing the PET image. A line connecting the two detection positions for the coincidence of the two annihilation photons is called a "Line of Response (LOR)". Alternatively, another arrangement is acceptable in which the coincidence list is generated by the console device 4.

Figure 3:
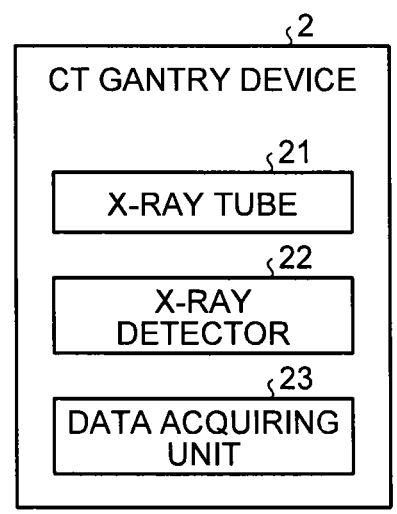
FIG. 3 is a drawing for explaining a configuration of a CT gantry device.

Returning to the description of FIG. 1, the CT gantry device 2 is a device that generates projection data of X-rays (hereinafter, "X-ray projection data") for reconstructing an X-ray CT image or for generating a scanogram, by detecting the X-rays transmitted through the patient P. FIG. 3 is a drawing for explaining a configuration of the CT gantry device.

As shown in FIG. 3, the CT gantry device 2 includes an X-ray tube 21, an X-ray detector 22, and a data acquiring unit 23. The X-ray tube 21 is a device that generates an X-ray beam and radiates the generated X-ray beam onto the patient P. The X-ray detector 22 is a device that detects, in a position opposite to the X-ray tube 21, the X-ray transmitted through the patient P. More specifically, the X-ray detector 22 is a two-dimensional-array-type detector that detects data indicating a two-dimensional intensity distribution of the X-ray transmitted through the patient P (hereinafter, "two-dimensional X-ray intensity distribution data). Even more specifically, the X-ray detector 22 is configured so that a plurality of rows of detecting elements each made up of X-ray detecting elements corresponding to a plurality of channels are arranged along the body-axis direction of the patient P. On the inside of the CT gantry device 2, the X-ray tube and the X-ray detector are supported by a rotating frame (not shown).

The data acquiring unit 23 is configured with a Data Acquisition System (DAS) and generates the X-ray projection data by performing an amplifying process and/or an Analogue/Digital (A/D) converting process on the two-dimensional X-ray intensity distribution data detected by the X-ray detector 22. Further, the data acquiring unit 23 transmits the X-ray projection data to the console device 4 shown in FIG. 1.

Figure 4:
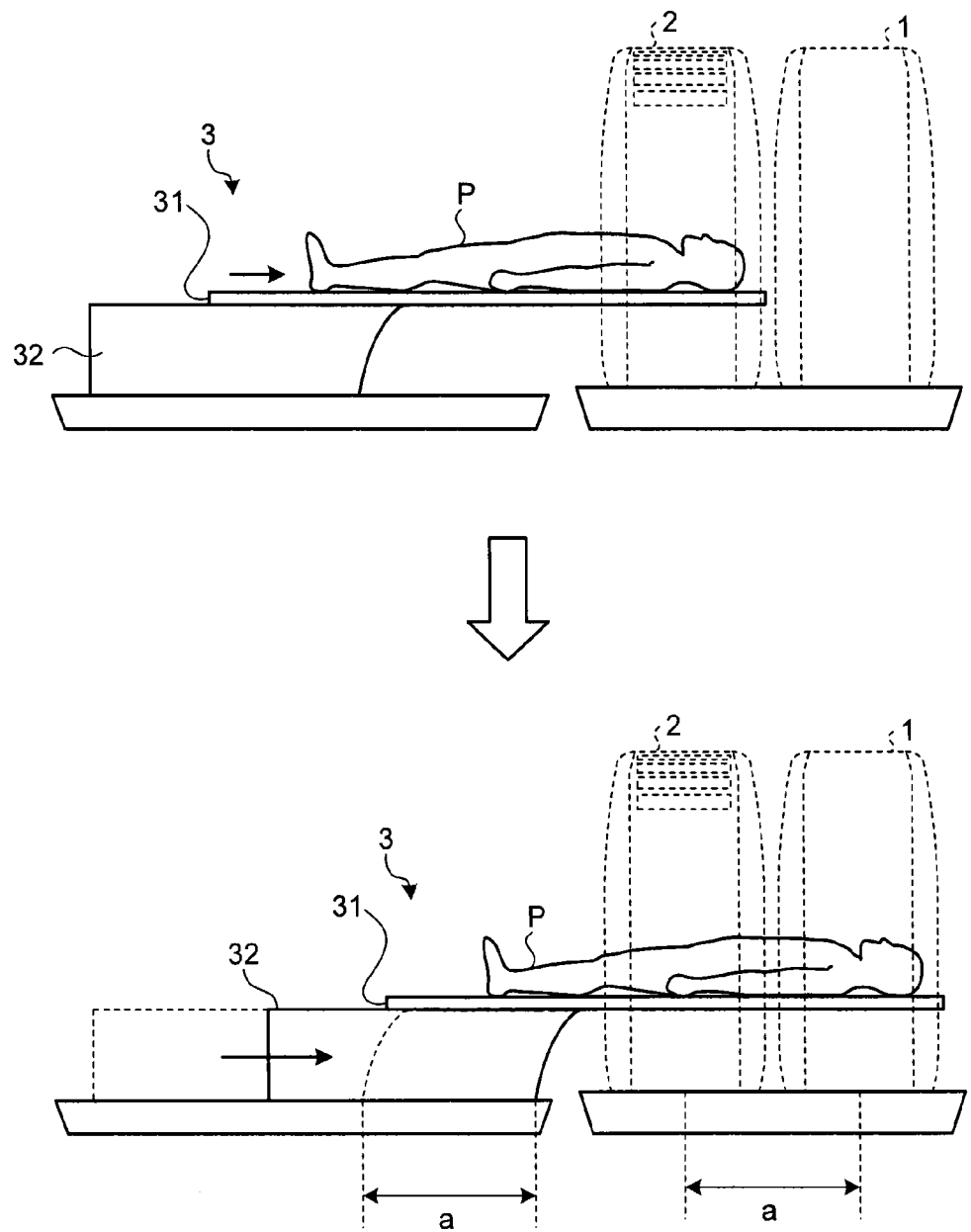
FIG. 4 is a drawing for explaining a couch device.

Returning to the description of FIG. 1, the couch device 3 is a bed on which the patient P is placed and includes a couchtop 31 and a couch 32. The couch device 3 is sequentially moved to image taking apertures of the CT gantry device 2 and of the PET gantry device 1, based on an instruction received from an operator of the PET-CT apparatus via the console device 4. In other words, by moving the couch device 3, the PET-CT apparatus first performs an X-ray CT image taking process and subsequently performs a PET image taking process. FIG. 4 is a drawing for explaining the couch device 3.

The couch device 3 moves the couchtop 31 and the couch 32 along the body-axis direction of the patient by using a driving mechanism (not shown). For example, while turning the rotating frame of the CT gantry device 2, the PET-CT apparatus moves the couchtop 31 horizontally in the direction toward the CT gantry device 2 as shown in the top part of FIG. 4, so that one or more X-ray CT images are taken by using a helical scanning method by which an image taking site of the patient P is helically and continuously scanned with X-rays.

Further, after having performed the X-ray CT image taking process, as shown in the bottom part of FIG. 4, the PET-CT apparatus inserts the image taking site of the patient P into the image taking aperture of the PET gantry device 1 by moving the couch 32 horizontally, while the couchtop 31 still protrudes from the couch 32. In this situation, as shown in the bottom part of FIG. 4, the couch 32 is moved a distance equal to the distance "a" between the center positions of the detectors of the PET gantry device 1 and the CT gantry device 2. In other words, by causing the couch 32 to move the distance "a", the protruding amount of the couchtop 31 from the couch 32 is arranged to be equal between the X-ray CT image taking process and the PET image taking process, when the images of mutually the same site of the patient P in terms of the body-axis direction are taken.

Further, the PET-CT apparatus performs a PET image taking process by moving the couchtop 31 horizontally in the opposite direction from the direction used during the X-ray CT image taking process. In this situation, the PET-CT apparatus takes images of a large portion of the patient by using a step-and-shoot method by which moving processes and image-taking processes are alternately repeated so that an image of a part of the patient is taken, and subsequently the patient is horizontally moved by a predetermined moving amount while the image taking process is stopped, before another image of a different part of the patient is taken.

Figure 5:
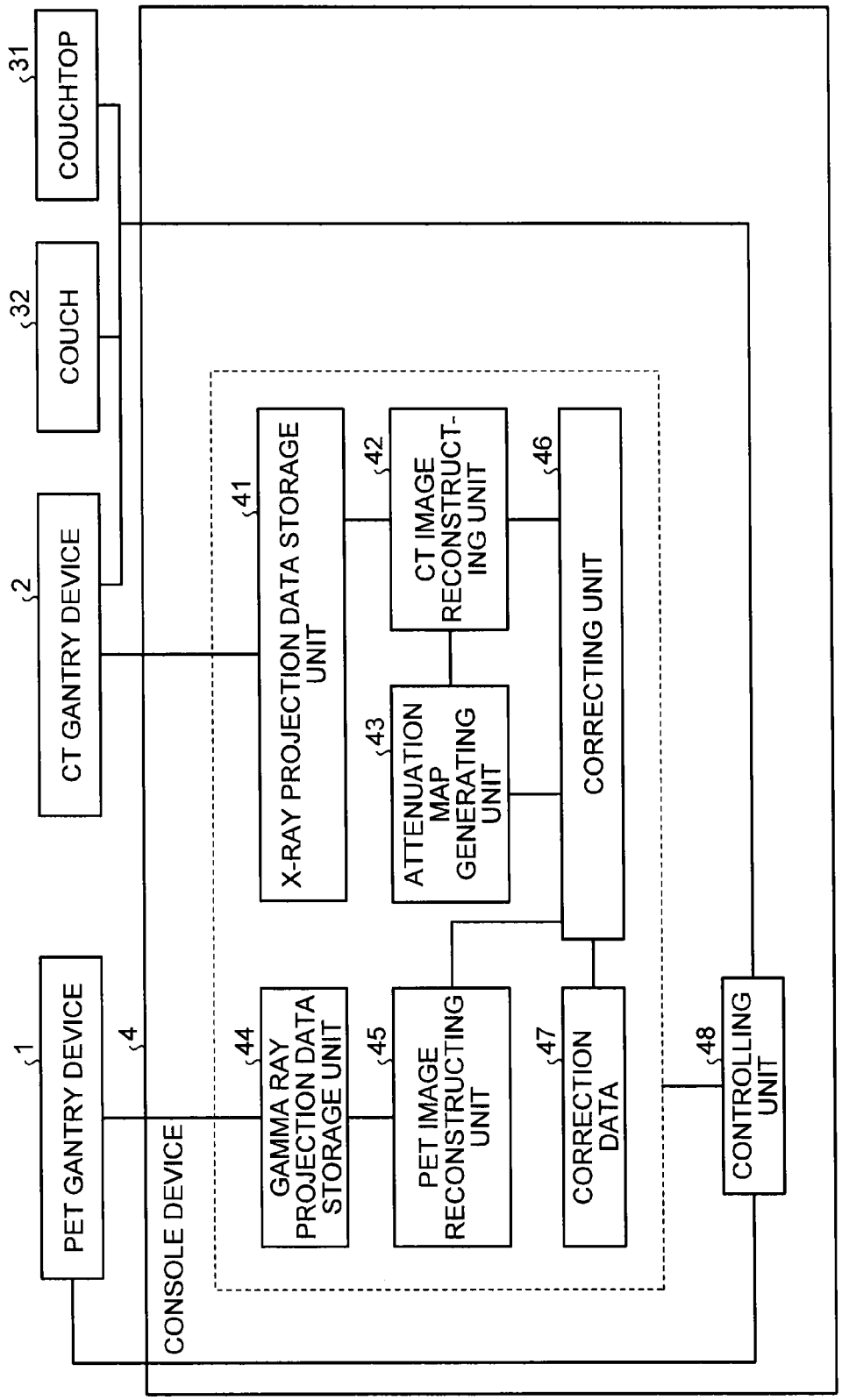
FIG. 5 is a drawing for explaining a configuration of a console device.

Returning to the description of FIG. 1, the console device 4 is a device that controls the image taking processes performed by the PET-CT apparatus by receiving instructions from the operator. FIG. 5 is a drawing for explaining a configuration of the console device.

As shown in FIG. 5, the console device 4 includes an X-ray projection data storage unit 41, a CT image reconstructing unit 42, an attenuation map generating unit 43, a gamma ray projection data storage unit 44, and a PET image reconstructing unit 45. Further, as shown in FIG. 5, the console device 4 includes a controlling unit 48 and correction data 47.

The X-ray projection data storage unit 41 stores therein the X-ray projection data transmitted from the data acquiring unit 23. More specifically, the X-ray projection data storage unit 41 stores therein the X-ray projection data used for reconstructing an X-ray CT image. The CT image reconstructing unit 42 reconstructs the X-ray CT image by, for example, using a Filtered Back Projection (FBP) method to perform a back projection process on the X-ray projection data to be reconstructed that is stored in the X-ray projection data storage unit 41.

In one example, during a whole-body medical examination using the PET-CT apparatus, the CT image reconstructing unit 42 reconstructs a plurality of X-ray CT images showing a plurality of cross sections that are orthogonal to the body-axis direction of the patient P, from the X-ray projection data, based on an image taking condition (e.g., a slice width) defined in an image taking plan.

The attenuation map generating unit 43 generates an attenuation map used for correcting an attenuation of the gamma rays occurring inside the patient P, by using the X-ray CT image reconstructed by the CT image reconstructing unit 42. The gamma ray projection data storage unit 44 stores therein the gamma ray projection data transmitted from the coincidence circuit 12. The PET image reconstructing unit 45 reconstructs the PET image from the gamma ray projection data stored in the gamma ray projection data storage unit 44, while using, for example, a successive approximation method.

A correcting unit 46 corrects the attenuation in the PET image by using the attenuation map generated by the attenuation map generating unit 43, and also, performs a correcting process when the X-ray CT image reconstructed by the CT image reconstructing unit 42 is combined with the PET image reconstructed by the PET image reconstructing unit 45. The correction data 47 stores therein processing results of the correcting unit 46. The processing performed by the correcting unit 46 and the correction data 47 will be explained in detail later.

The controlling unit 48 controls processing in the entirety of the PET-CT apparatus. More specifically, the controlling unit 48 controls the image taking processes performed by the PET-CT apparatus by controlling the PET gantry device 1, the CT gantry device 2, the couchtop 31, and the couch 32.

Further, the controlling unit 48 controls processing performed by the PET image reconstructing unit 45 that uses the data stored in the gamma ray projection data storage unit 44. Also, the controlling unit 48 controls processing performed by the CT image reconstructing unit 42 and the attenuation map generating unit 43 that use the data stored in the X-ray projection data storage unit 41. Furthermore, the controlling unit 48 controls processing performed by the correcting unit 46. The controlling unit 48 receives instructions from the operator via an input/output device (not shown). Further, the controlling unit 48 exercises control so that a Graphical User Interface (GUI) used by the operator to input the instructions while using the input/output device (not shown), as well as the X-ray CT image and the PET image are displayed.

The overall configuration of the PET-CT apparatus according to the first embodiment has thus been explained. The PET-CT apparatus according to the first embodiment configured as described above performs a correcting process related to aligning the positions of images taken by using the step-and-shoot method and images taken by the helical scanning method.

More specifically, the PET-CT apparatus according to the first embodiment performs a correcting process to correct positional gaps in the images between the PET images and the X-ray CT images that are caused by sloping down of the couchtop 31 due to the weight applied by the patient P. In the following sections, the state in which the couchtop 31 is sloping down may be referred to as "couchtop sagging".

Next, the positional gaps in the images that are caused by the couchtop sagging, between the images taken by using the step-and-shoot method and the images taken by using the helical scanning method will be explained. In the following sections, impacts of the couchtop sagging on the images taken by using the mutually-different image taking methods will be explained first. After that, the positional gaps between the images will be explained.

Figure 6:
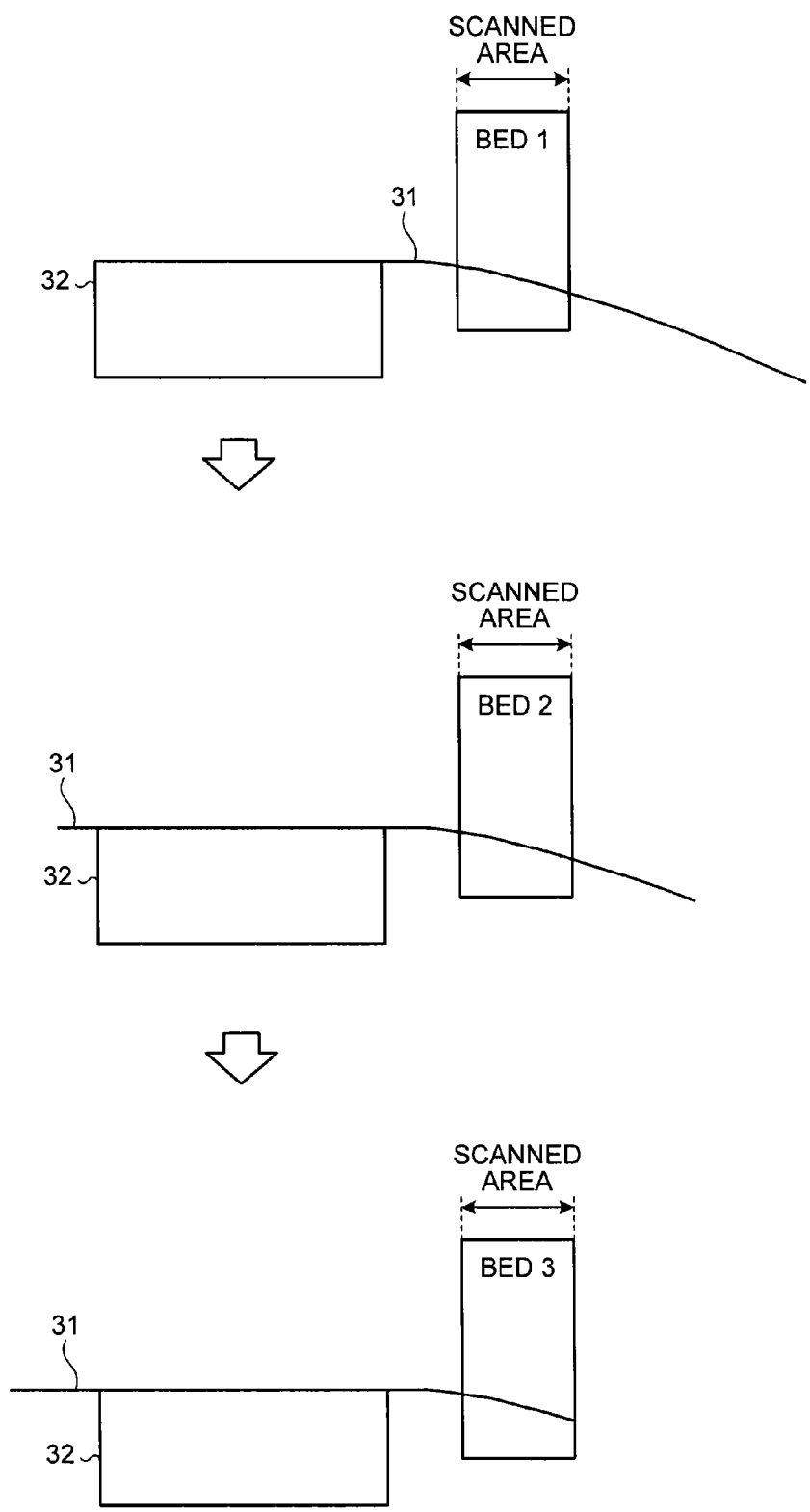
FIG. 6 is a drawing for explaining couchtop sagging in images taken by using a step-and-shoot method.

FIG. 6 is a drawing for explaining the couchtop sagging in the images taken by using the step-and-shoot method. Shown in FIG. 6 is couchtop sagging that is observed when the couch 32 is moved toward the PET gantry device 1, before PET images are taken while returning the protruding couchtop 31 to the couch 32 by using the step-and-shoot method. The scanned areas in FIG. 6 are the scanned areas of the PET gantry device 1. In FIG. 6, "bed 1", "bed 2", and "bed 3" indicate the image taking positions of the PET images taken by using the step-and-shoot method. In other words, in FIG. 6, a scanning process is performed so as to take a plurality of tomographic images at the image taking positions "bed 1", "bed 2", and "bed 3", respectively. Although the patient is not drawn in FIG. 6, the couchtop sagging observed while the patient is placed on the couchtop 31 is actually shown.

As shown in FIG. 6, the degree of the couchtop sagging varies depending on the protruding amount of couchtop 31 from the couch 32. In other words, as shown in the top part of FIG. 6, when the bed 1 is scanned, the impact of the patient's weight on the couchtop 31 is larger, and the degree of the couchtop sagging in the scanned area is also higher. In contrast, as shown in the middle and the bottom parts of FIG. 6, as the protruding amount of the couchtop 31 from the couch 32 decreases, the impact of the patient's weight on the couchtop 31 decreases, and the degree of the couchtop sagging in the scanned area also becomes lower.

Figure 7:
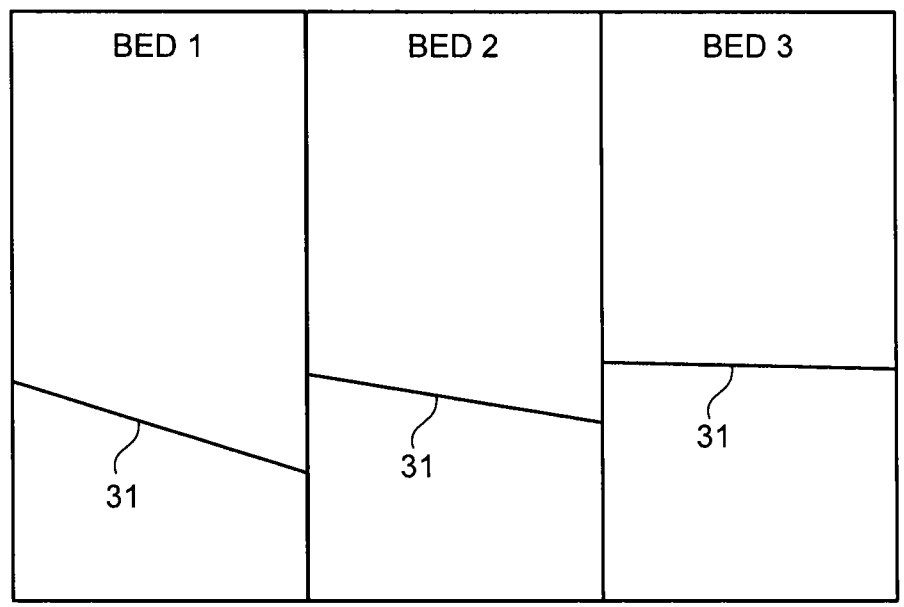
FIG. 7 is a drawing for explaining couchtop positions in images taken by using the step-and-shoot method.

FIG. 7 is a drawing for explaining couchtop positions in the images taken by using the step-and-shoot method. In FIG. 7, sagittal planes of the taken images corresponding to the different beds are shown. In other words, cross sections along the body-axis direction of the patient are shown in FIG. 7. When the images are taken by using the step-and-shoot method, the position of the couchtop 31 exhibits height differences among the beds as shown in FIG. 7, because the degree of the couchtop sagging is different for each of the beds.

Figure 8:
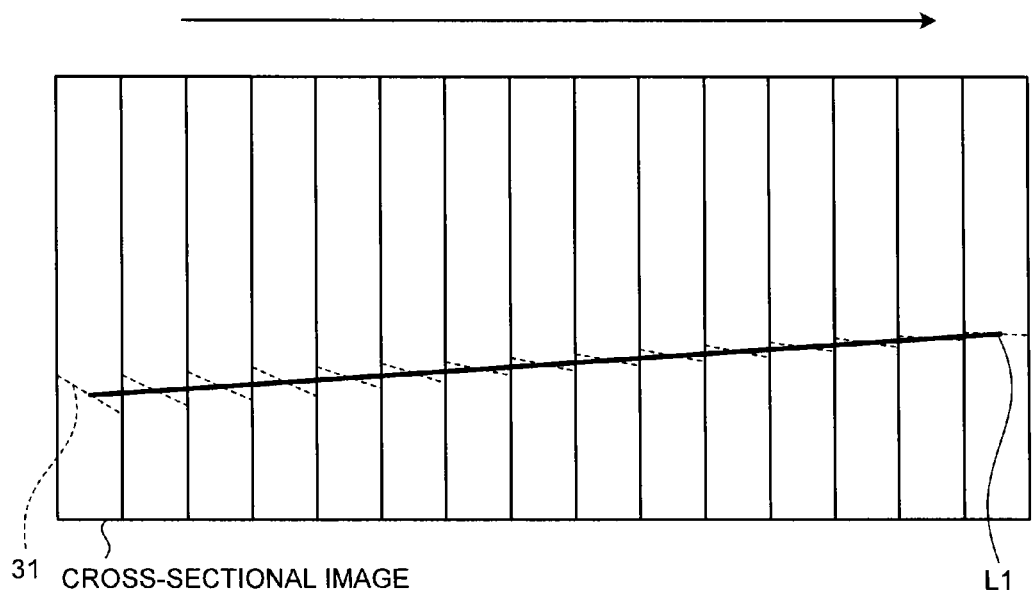
FIG. 8 is a drawing for explaining couchtop positions in images taken by using a helical scanning method.

FIG. 8 is a drawing for explaining couchtop positions in the images taken by using the helical scanning method. In FIG. 8, the couchtop positions are shown that are observed when CT images are taken while the couchtop 31 is continuously caused to protrude by using the helical scanning method. In FIG. 8, sagittal plane images generated by using a plurality of cross-sectional images taken while using the helical scanning method are shown. The arrow in FIG. 8 indicates the moving direction of the couchtop 31. The plurality of rectangles in FIG. 8 indicate the slice widths of the cross-sectional images. The straight line L1 in FIG. 8 indicates the straight line that goes through the center of the couchtop 31 in the cross-sectional images.

When the images are taken by using the helical scanning method, the position of the couchtop 31 in the cross-sectional images gradually lowers in accordance with the increase in the protruding amount of the couchtop 31, as indicated by the straight line L1 in FIG. 8, because the degree of the couchtop sagging becomes higher in proportion to the increase in the protruding amount of the couchtop 31. In this situation, the slice widths of the CT images taken by using the helical scanning method that are viewed on the sagittal planes are very thin in actuality, and are not so thick as depicted in FIG. 8. Thus, if the width of each of the cross-sectional images shown in FIG. 8 is infinitely decreased (i.e., if the slice widths are reduced close to 0), the cross-sectional images converge at the center of the X-ray detector 22. Accordingly, the straight line L1 that goes through the center of the couchtop 31 rendered in the cross-sectional images is the couchtop position in the images taken by using the helical scanning method.

Figure 9:
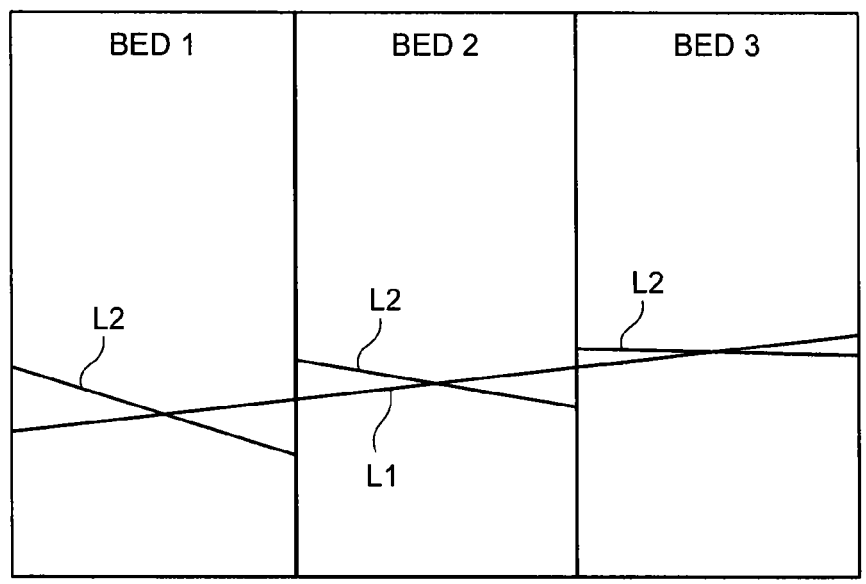
FIG. 9 is a drawing for explaining positional gaps between images taken by using the step-and-shoot method and images taken by using the helical scanning method.

FIG. 9 is a drawing for explaining positional gaps between images taken by using the step-and-shoot method and images taken by using the helical scanning method. In this situation, FIG. 9 shows the couchtop positions (the straight lines L2) in the images taken by using the step-and-shoot method shown in FIG. 7 and the couchtop positions (the straight lines L1) in the images taken by using the helical scanning method shown in FIG. 8.

As indicated by the straight lines L1 and L2 in FIG. 9, positional gaps are observed in the positions of the couchtop between the images taken by using the mutually-different image taking methods because the gradients are different. In other words, the couchtop sagging causes the positional gaps between the images taken by using the mutually-different image taking methods. The positional gaps deteriorate the precision level of the images generated by the PET-CT apparatus or the like.

For example, the PET-CT apparatus uses CT images to perform an attenuation correcting process and/or a scattering correcting process on PET images. In this situation, if there is a positional gap between the PET images and the CT images, it is not possible to perform the correcting processes accurately. Further, a fusion image generated by the PET-CT will also have a positional gap, which makes it difficult for a person to interpret the fusion image.

Figure 10:
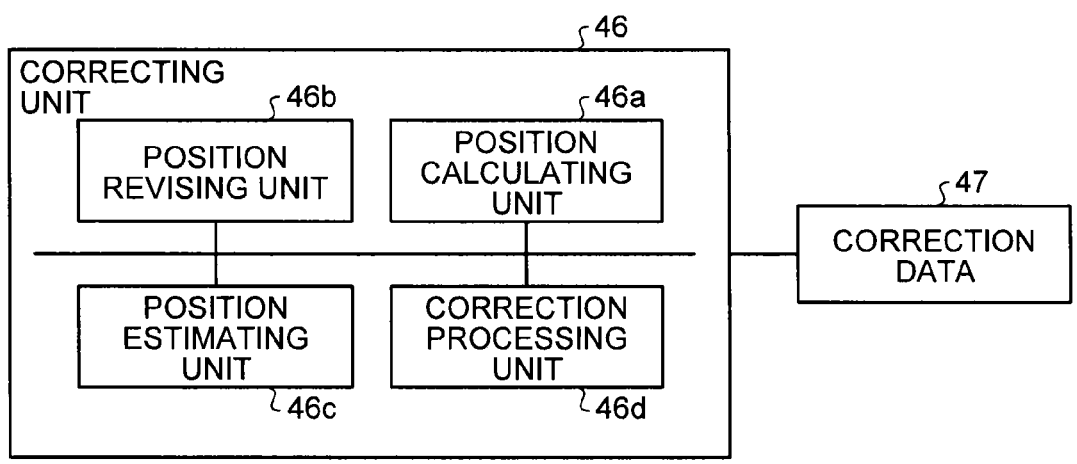
FIG. 10 is a drawing for explaining a configuration of a correcting unit according to the first embodiment.

To cope with this situation, the PET-CT apparatus according to the first embodiment is configured to make it possible to inhibit the deterioration of the precision level of the images even if couchtop sagging occurs, with a correcting process performed by the correcting unit 46 described in detail below. FIG. 10 is a drawing for explaining a configuration of the correcting unit 46 according to the first embodiment. As shown in FIG. 10, the correcting unit 46 includes a position calculating unit 46a, a position revising unit 46b, a position estimating unit 46c, and a correction processing unit 46d. Further, the correcting unit 46 stores processing results into the correction data 47.

In the plurality of images taken by using the helical scanning method, the position calculating unit 46a calculates a position of a structure that is rendered in the images, is linear with respect to the body-axis direction, and exhibits a behavior identical to the sloping down of the couchtop. More specifically, the position calculating unit 46a detects the couchtop rendered in each of the plurality of X-ray CT images of the patient tomographically taken by the X-ray CT apparatus and calculates the position of the couchtop detected in each of the X-ray CT images.

Figure 11:
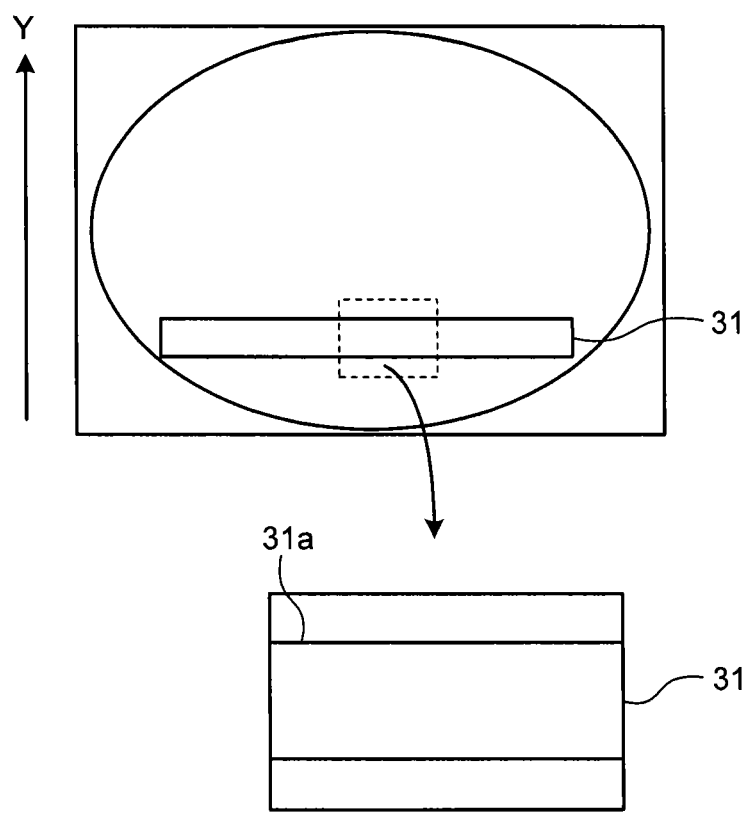
FIG. 11 is a drawing that schematically illustrates an exemplary process performed by a position calculating unit according to the first embodiment.

FIG. 11 is a drawing that schematically illustrates an exemplary process performed by the position calculating unit 46a according to the first embodiment. Shown in FIG. 11 is a cross-sectional image taken by using the helical scanning method and reconstructed from X-ray projection data by the CT image reconstructing unit 42. As shown in FIG. 11, for example, the position calculating unit 46a first detects the couchtop 31 rendered in the cross-sectional image and cuts out an area containing the detected couchtop 31. Further, the position calculating unit 46a calculates a Y-axis-direction coordinate of a surface 31a of the couchtop 31 contained in the cut-out area.

In one example, the position calculating unit 46a assigns a number to each of the pixels in the Y-axis direction of the cross-sectional image and obtains the number assigned to the pixel rendering the surface 31a of the couchtop 31 as the Y-axis-direction coordinate. Further, the position calculating unit 46a performs the couchtop detecting process and the couchtop position calculating process on each of all the cross-sectional images reconstructed from the X-ray projection data by the CT image reconstructing unit 42. In this situation, the position calculating unit 46a detects the couchtop in the images by employing, for example, a method that uses profiles of the images and/or a pattern matching method that uses a template having the shape of the couchtop.

Returning to the description of FIG. 10, the position revising unit 46b judges whether the couchtop position calculated by the position calculating unit 46a is wrong in each of the cross-sectional images. When having determined that a couchtop position is wrong, the position revising unit 46b revises the couchtop position. More specifically, when a value indicating the couchtop position calculated by the position calculating unit 46a exceeds an estimated value by a value larger than a predetermined threshold value, the position revising unit 46b determines that the value indicating the couchtop position is wrong.

FIG. 12 is a drawing that schematically illustrates an exemplary process performed by the position revising unit 46b. In FIG. 12, the vertical axis expresses the couchtop position calculated from the pixel numbers. Also, in FIG. 12, the horizontal axis expresses the slices, which are the parts at each of which one X-ray CT image is taken. In other words, FIG. 12 indicates the couchtop position calculated by the position calculating unit 46a for each of the slices.

For example, when the position calculating unit 46a has calculated the couchtop position shown in the top part of FIG. 12, the position revising unit 46b estimates possible values of the couchtop position, based on the values of the couchtop positions corresponding to the slices. For example, the position revising unit 46b estimates the possible values of the couchtop position by calculating an approximation (e.g., by using a least-squares method) while using a polynomial based on the values of the couchtop position corresponding to the slices. Further, the position revising unit 46b compares the estimated values with the values calculated by the position calculating unit 46a. If the difference between two values exceeds the predetermined threshold value, the position revising unit 46b determines that the value calculated by the position calculating unit 46a is wrong.

For example, if the predetermined threshold value is "1 pixel", because the value "r" shown in the top part of FIG. 12 exceeds "1 pixel", the position revising unit 46b determines that the value of the position "P1" is wrong. The value "r" shown in the top part of FIG. 12 indicates the difference between the value on an approximation curve (not shown) calculated by the position revising unit 46b and the value of the position "P1". Further, as shown in the bottom part of FIG. 12, the position revising unit 46b revises the value of the position "P1" so as to be the value on the approximation curve (not shown). Similarly, as shown in the bottom part of FIG. 12, the position revising unit 46b revises each of the values of the positions "P2" and "P3" shown in the top part of FIG. 12 so as to be a value on the approximation curve (not shown).

In the example above, a situation is explained in which the revisions are made only for such values whose difference between a value on the approximation curve and the value calculated by the position calculating unit 46a exceeds the predetermined threshold value. However, the features disclosed herein are not limited to this example. For example, it is acceptable to revise each of all the values calculated by the position calculating unit 46a by replacing each value with a value on the approximation curve.

Returning to the description of FIG. 10, the position estimating unit 46c estimates the couchtop position in the images taken by using the step-and-shoot method, based on the couchtop positions in the images taken by using the helical scanning method. More specifically, the position estimating unit 46c first calculates a gradient of the couchtop for each of the beds in the X-ray CT images, by using the values of the couchtop positions in the X-ray CT images revised by the position revising unit 46b. Subsequently, the position estimating unit 46c calculates a gradient of the couchtop in the PET images taken by using the step-and-shoot method, based on the calculated gradients of the couchtop in the X-ray CT images. After that, the position estimating unit 46c estimates the positions of the couchtop, based on the calculated gradients of the couchtop. In the following sections, an example will be explained in which the couchtop positions are estimated by applying a negative-scaling method to the gradients of the couchtop in the X-ray CT images.

For example, the position estimating unit 46c calculates the gradients of the couchtop in the PET images by using Expression (1) shown below. In Expression (1), "$\text{grad}_{PET}(z)$" denotes a gradient of the couchtop in a PET image expressed by using "z" as a variable. Also, in Expression (1), "$\text{grad}_{CT}$" denotes a gradient of the couchtop in an X-ray CT image. Further, "$\text{grad}_{init}$" in Expression (1) denotes an initial gradient of the couchtop without any weight applied thereto (hereinafter, the initial gradient of the couchtop without any weight applied thereto will be referred to as a "reference line gradient"). Further, "A(z)" in Expression (1) denotes a function that uses "z" as a variable.

$$\text{grad}_{PET}(z) = A(z) \times \text{grad}_{CT} + 2 \times \tan(\text{grad}_{init}) \qquad (1)$$

As shown in Expression (1), the position estimating unit 46c calculates each of the gradients of the couchtop in the PET images by multiplying each of the gradients of the couchtop in the X-ray CT images by the variable and further adding a value double the tangent (i.e., the reference line gradient) thereto. For example, the position estimating unit 46c uses a variable related to the couchtop protruding amount and the couchtop sagging as the value z. Alternatively, it is acceptable for the position estimating unit 46c to calculate the gradients of the couchtop in the PET images by using Expression (2) shown below. In Expression (2), "A" denotes an arbitrary constant.

$$\text{grad}_{PET} = A \times \text{grad}_{CT} + 2 \times \tan(\text{grad}_{init}) \quad (2)$$

In other words, as shown in Expression (2), the position estimating unit 46c calculates each of the gradients of the couchtop in the PET images by multiplying each of the gradients of the couchtop in the X-ray CT images by the arbitrary constant. For example, the position estimating unit 46c calculates each of the gradients of the couchtop in the PET images by using Expression (3) shown below.

$$\text{grad}_{PET} = -1 \times \text{grad}_{CT} + 2 \times \tan(\text{grad}_{init}) \quad (3)$$

For example, as shown in Expression (3), the position estimating unit 46c calculates each of the gradients of the couchtop in the PET images by multiplying each of the gradients of the couchtop in the X-ray CT images by "−1". In this situation, the variable or the constant by which each of the gradients of the couchtop in the X-ray CT images is to be multiplied is arbitrarily determined by a designer or an operator of the PET-CT apparatus. In those situations, for example, by taking images with the CT gantry device 2 using the helical scanning method and the step-and-shoot method, it is possible to determine the variable or the constant in advance, based on the couchtop positions rendered in the taken images.

Figure 13:
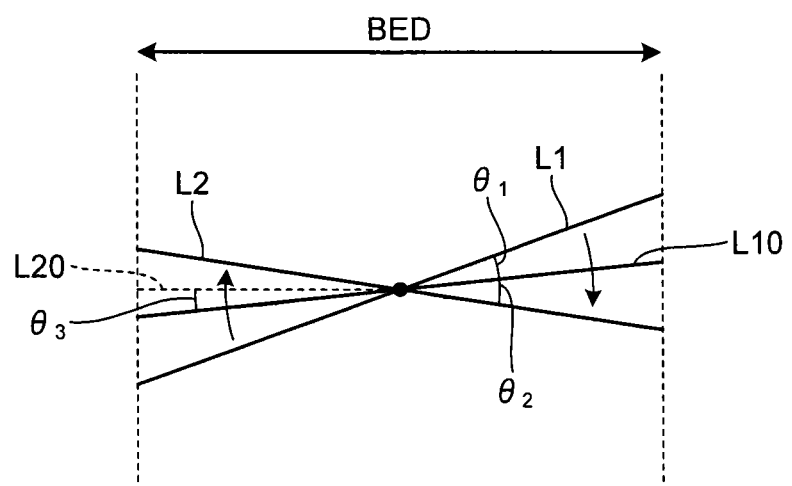
FIG. 13 is a drawing that schematically illustrates an exemplary process performed by a position estimating unit.

FIG. 13 is a drawing that schematically illustrates an exemplary process performed by the position estimating unit 46c. For example, as shown in FIG. 13, the position estimating unit 46c calculates the gradient of the straight line L1 as the gradient of the couchtop in the X-ray CT image for each of the beds. Further, the position estimating unit 46c calculates the gradient of the couchtop in a PET image by using the calculated gradient of the straight line L1 and one of Expressions (1) to (3) shown above. After that, as shown in FIG. 13, the position estimating unit 46c estimates the couchtop position in the PET image to be a straight line L2 that intersects the straight line L1 in the slice at the center of the bed and of which the gradient is equal to the calculated gradient.

In this situation, the couchtop position in the PET image estimated by the position estimating unit 46c is the couchtop position in which the reference line is taken into account because one of the expressions shown above is used. As mentioned above, the reference line is the line indicating the initial gradient of the couchtop without any weight applied thereto. It might be ideal if the couchtop slid on a level plane when no weight is applied thereto; however, in actuality, the couchtop is designed so as to slightly rise when no weight is applied thereto so that the couchtop becomes level when a patient is placed thereon. For this reason, to take the rise into account, the couchtop positions are estimated by using the reference line according to the first embodiment.

For example, as shown in FIG. 13, the position estimating unit 46c estimates a straight line indicating the couchtop position in a PET image to be a straight line L2 obtained by turning the straight line L1 indicating the couchtop position in an X-ray CT image with respect to a straight line L10 serving as the reference line. The dotted line L20 in FIG. 13 indicates the level plane. Also, in FIG. 13, $\theta_1$ denotes the angle between the straight line L1 and the straight line L10 serving as the reference line. Further, $\theta_2$ in FIG. 13 denotes the angle between the straight line L2 and the straight line L10 serving as the reference line. Also, $\theta_3$ in FIG. 13 denotes the angle between the straight line L1 and the dotted line L4 indicating the level plane.

In other words, the position estimating unit 46c calculates the value of "$\theta_2$" in FIG. 13 from the values of "$\theta_1$" and "$\theta_3$" and estimates the couchtop position in the PET image to be the straight line L2 sloped by the value "$\theta_2$" calculated from the reference line L10.

As explained above, the PET-CT apparatus according to the first embodiment is configured so as to move the couch 32 the distance equal to the distance between the center positions of the detectors in the PET gantry device 1 and the CT gantry device 2. In other words, at the centers of the detectors, the degrees of the couchtop sagging are equal, and the couchtop positions in the Y-axis direction are also equal. Accordingly, the position estimating unit 46c is able to estimate the couchtop position in each of the PET images to be the straight line L2 that intersects the straight line L1 in the slice at the center of the bed and of which the gradient is equal to the calculated gradient.

Returning to the description of FIG. 10, based on the couchtop positions in the plurality of PET images estimated by the position estimating unit 46c, the correction processing unit 46d calculates correction amounts used for correcting the positional gaps between the X-ray CT images and the PET images. Further, the correction processing unit 46d corrects the positional gaps between the X-ray CT images and the PET images by using the calculated correction amounts.

More specifically, the correction processing unit 46d calculates a Y-axis-direction moving amount for each set of slices in substantially the same position of the patient, based on the couchtop positions in the plurality of PET images estimated by the position estimating unit 46c and the couchtop positions in the plurality of X-ray CT images already revised by the position revising unit 46b. Further, the correction processing unit 46d corrects the positions of the X-ray CT images with respect to the PET images and corrects the positions of the PET images with respect to the X-ray CT images.

In the following sections, a process performed by the PET-CT apparatus according to the first embodiment to generate combined images from X-ray CT images and PET images will be explained. First, the PET-CT apparatus according to the first embodiment is configured so that, when a CT examination and a PET examination have been performed on the patient P, the CT image reconstructing unit 42 reconstructs X-ray CT images by using the X-ray projection data stored in the X-ray projection data storage unit 41. In this situation, the X-ray CT images reconstructed by the CT image reconstructing unit 42 are stored into the correction data 47.

The position calculating unit 46a calculates the couchtop positions for the plurality of X-ray CT images reconstructed by the CT image reconstructing unit 42. Further, the position revising unit 46b revises the couchtop positions in the plurality of X-ray CT images calculated by the position calculating unit 46a. After that, the position estimating unit 46c estimates the couchtop positions in the plurality of PET images, based on the couchtop positions in the plurality of X-ray CT images already revised by the position revising unit 46b. In this situation, the couchtop positions in the plurality of X-ray CT images already revised by the position revising unit 46b and the couchtop positions in the plurality of PET images estimated by the position estimating unit 46c are stored into the correction data 47.

The correction processing unit 46d reads the couchtop positions in the plurality of X-ray CT images and the couchtop positions in the plurality of PET images that are stored in the correction data 47 and calculates a Y-axis-direction moving amount for each set of slices in substantially the same position of the patient. Further, the correction processing unit 46d performs the correcting process to align the positions of the plurality of X-ray CT images reconstructed by the CT image reconstructing unit 42 with the PET images. In this situation, the Y-axis-direction moving amount for each set of slices in substantially the same position of the patient calculated by the correction processing unit 46d is stored into the correction data 47.

FIG. 14 is a drawing that schematically illustrates an exemplary process performed by the correction processing unit 46d to align the positions of the X-ray CT images with the PET images. For example, as shown in FIG. 14, the correction processing unit 46d calculates a moving amount for each slice for each of beds 1, 2, and 3, based on the couchtop positions L1 in the X-ray CT images already revised by the position revising unit 46b and the couchtop positions L2 in the PET images estimated by the position estimating unit 46c.

After that, the correction processing unit 46d slides the X-ray CT image for each slice so as to align the position thereof with a PET image, so that the couchtop positions L1 of the X-ray CT images match the couchtop positions L2 of the PET images. Subsequently, the correction processing unit 46d stores the X-ray CT images on which the position aligning process has been performed, into the correction data 47.

The attenuation map generating unit 43 reads the X-ray CT images on which the position aligning process was performed and that are stored in the correction data 47 and generates an attenuation map by using the read X-ray CT images. In this situation, the attenuation map generated by the attenuation map generating unit 43 is stored into the correction data 47.

The PET image reconstructing unit 45 reconstructs PET images by using the gamma ray projection data stored in the gamma ray projection data storage unit 44 and the attenuation map stored in the correction data 47. In other words, the PET image reconstructing unit 45 reconstructs the PET images by using the attenuation map in which the positional gaps between the images are corrected. In this situation, the PET images reconstructed by the PET image reconstructing unit 45 are stored into the correction data 47.

When the PET images are reconstructed by the PET image reconstructing unit 45, the correction processing unit 46d reads the PET images stored in the correction data 47 and performs a correcting process to align the positions of the read PET images with the X-ray CT images reconstructed by the CT image reconstructing unit 42.

Figure 15:
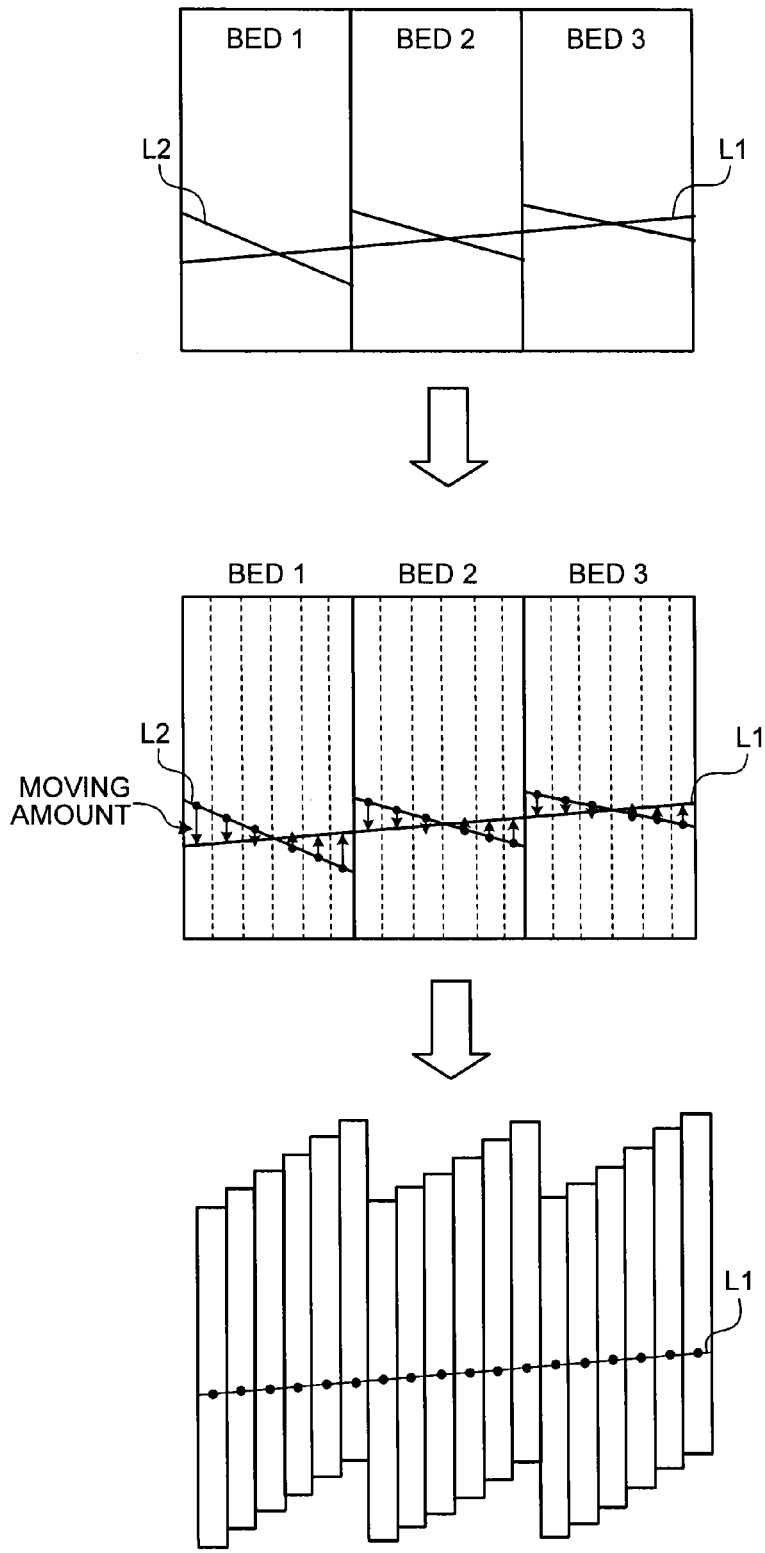
FIG. 15 is a drawing that schematically illustrates an exemplary process performed by the correction processing unit to align positions of PET images with X-ray CT images.

More specifically, the correction processing unit 46d reads the X-ray CT images, the PET images, and the Y-axis-direction moving amount for each set of slices for substantially the same position of the patient that are stored in the correction data 47 and performs the correcting process to align the positions of the PET images with the X-ray CT images. FIG. 15 is a drawing that schematically illustrates an exemplary process performed by the correction processing unit 46d to align the positions of the PET images with the X-ray CT images.

For example, as shown in FIG. 15, the correction processing unit 46d performs a positional aligning process to cause the couchtop positions L2 in the PET images match the couchtop positions L1 in the X-ray CT images, by moving the PET image by the moving amount for each of the slices. Further, the correction processing unit 46d stores the PET images on which the position aligning process was performed, into the correction data 47.

Based on an instruction from the operator of the PET-CT apparatus that is input via the input unit (not shown), the controlling unit 48 reads, for example, the X-ray CT images reconstructed by the CT image reconstructing unit 42 and the PET images of which the positions were aligned with the X-ray CT images that are stored in the correction data 47, and causes a display unit (not shown) to display images obtained by combining the X-ray CT images and the PET images that are read.

As explained above, by estimating the couchtop position in the PET images based on the couchtop positions in the X-ray images and performing the image correcting process so that the one couchtop position matches the other couchtop position, the PET-CT apparatus according to the first embodiment makes it possible to inhibit the deterioration of the precision level of the images, even if there is a positional gap between the images taken by using the mutually-different image taking methods.

Next, a process performed by the PET-CT apparatus according to the first embodiment will be explained, with reference to FIG. 16. FIG. 16 is a flowchart of an image processing procedure performed by the PET-CT apparatus according to the first embodiment. Shown in FIG. 16 is processing that is performed after an X-ray CT examination using the helical scanning method and a PET examination using the step-and-shoot method have been performed on a patient. As shown in FIG. 16, in the PET-CT apparatus according to the first embodiment, the CT image reconstructing unit 42 reconstructs X-ray CT images by using the X-ray projection data stored in the X-ray projection data storage unit 41 (step S101).

Subsequently, the correcting unit 46 corrects positional gaps of the X-ray CT images with respect to the PET images (step S102). After that, the attenuation map generating unit 43 generates an attenuation map by using the corrected X-ray CT images (step S103). Further, the PET image reconstructing unit 45 reconstructs PET images by using the attenuation map generated by the attenuation map generating unit 43 and the gamma ray projection data stored in the gamma ray projection data storage unit 44 (step S104).

Subsequently, the correcting unit 46 corrects positional gaps of the PET images with respect to the X-ray CT images (step S105). After that, the controlling unit 48 combines the corrected PET images with the X-ray CT images generated by the CT image reconstructing unit 42 and causes a display device (not shown) to display fusion images (step S106), and the process is thus ended.

Next, the process to correct an X-ray CT image performed by the PET-CT apparatus according to the first embodiment will be explained, with reference to FIG. 17. FIG. 17 is a flowchart of a correcting process procedure performed on an X-ray CT image by the PET-CT apparatus according to the first embodiment. The process shown in FIG. 17 corresponds to the process at step S102 shown in FIG. 16.

As shown in FIG. 17, in the PET-CT apparatus according to the first embodiment, the position calculating unit 46a cuts out an area in which the couchtop is rendered in the X-ray CT image (step S201) and calculates a couchtop position (step S202).

Subsequently, the position revising unit 46b revises a wrong calculation of the couchtop position in the X-ray CT image calculated by the position calculating unit 46a (step S203). After that, the position estimating unit 46c estimates the couchtop position in a PET image, based on the couchtop position in the X-ray CT image (step S204). After that, the correction processing unit 46d calculates a correction amount, based on the couchtop position in the X-ray CT image and the couchtop position in the PET image estimated by the position estimating unit 46c (step S205). The correction processing unit 46d corrects the X-ray CT image so as to be in the position of the PET image, based on the calculated correction amount (step S206), and the process is thus ended.

As explained above, according to the first embodiment, the position calculating unit 46a calculates the couchtop position rendered in each of the X-ray CT images of the patient that are tomographically taken while the couchtop is continuously moved along the body-axis direction. The position estimating unit 46c estimates the couchtop position calculated by the calculating unit for each of the PET images of the patient that are tomographically taken by moving the patient by a predetermined distance at a time, along the body-axis direction. Based on the couchtop position calculated by the position calculating unit 46a and the couchtop position estimated by the position estimating unit 46c, the correction processing unit 46d aligns the positions of the X-ray CT image and the PET image that are obtained by taking images of substantially the same position of the patient. Accordingly, the PET-CT apparatus according to the first embodiment makes it possible to inhibit the deterioration of the precision level of the images caused by the positional gaps in the images taken by using the mutually-different image taking methods.

Figure 18A:
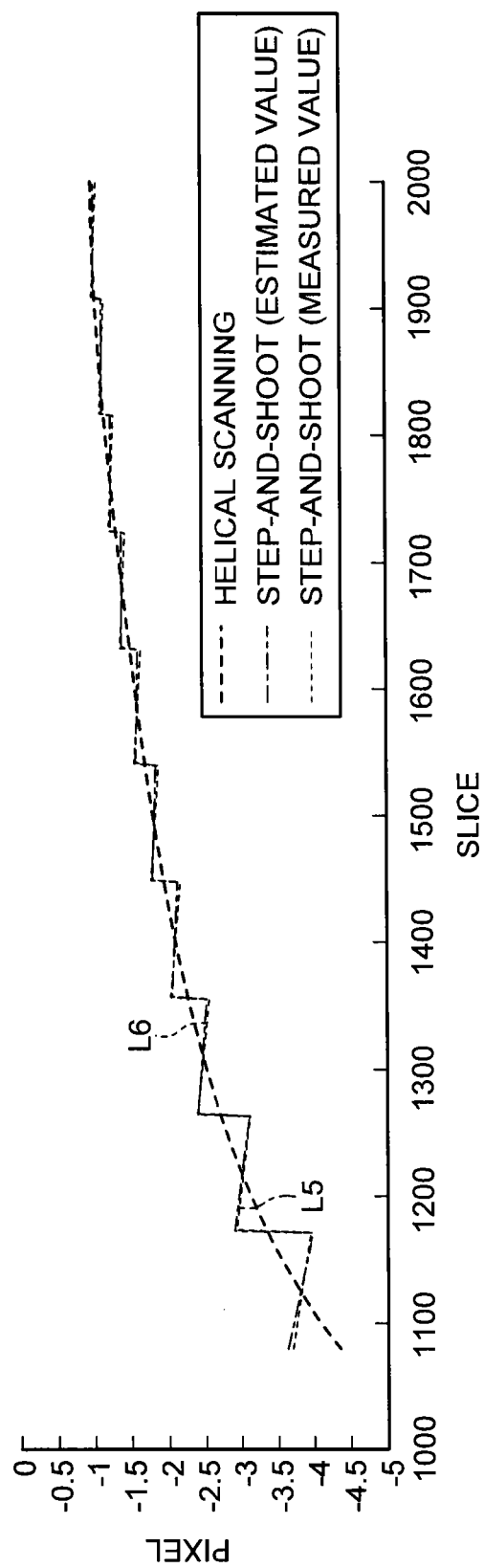
FIG. 18A is a chart of a simulation result obtained when a 120-kilogram weight is applied to a couchtop.

Next, simulation results will be explained, with reference to FIGS. 18A and 18B. FIG. 18A is a chart of a simulation result obtained when a 120-kilogram weight is applied to a couchtop. FIG. 18B is a chart of a simulation result obtained when a 200-kilogram weight is applied to a couchtop. Shown in FIGS. 18A and 18B are measurement results obtained by using an X-ray CT apparatus to measure the couchtop positions during an image taking process using the helical scanning method and the couchtop positions during an image taking process using the step-and-shoot method and an estimation result obtained by using the disclosed technique to estimate the couchtop positions during an image taking process using the step-and-shoot method. The X-ray CT apparatus is configured to be able to take images using the helical scanning method and the step-and-shoot method.

The vertical axes in FIGS. 18A and 18B express pixels. The horizontal axes in FIGS. 18A and 18B express slices. Further, "step-and-shoot (estimated value)" in each of FIGS. 18A and 18B denotes the estimation result obtained by using the disclosed technique. In contrast, "step-and-shoot (measured value)" in each of FIGS. 18A and 18B denotes the measurement result measured by using the X-ray CT apparatus.

As shown in FIGS. 18A and 18B, in both situations where the 120-kilogram weight was applied and where the 200-kilogram weight was applied, the line L5 indicating the "step-and-shoot (estimated value)" and the line L6 indicating the "step-and-shoot (measured value)" overlap each other almost entirely. In other words, by using the disclosed technique, it is possible to estimate, with a high level of precision, the couchtop positions during the step-and-shoot image taking processes and to inhibit the deterioration of the precision level of the images caused by the positional gaps between the images taken by using the mutually-different image taking methods.

Further, according to the first embodiment, the position calculating unit 46a calculates the Y-axis-direction position of the couchtop. Accordingly, the PET-CT apparatus according to the first embodiment is able to correct the positional gaps caused by the couchtop sagging between the images taken by using the helical scanning method and the images taken by using the step-and-shoot method and thus makes it possible to inhibit the deterioration of the precision level of the images caused by the positional gaps between the images taken by using the mutually-different image taking methods.

Further, according to the first embodiment, the position revising unit 46b revises the couchtop positions in the X-ray CT images, based on the couchtop position in each of the plurality of X-ray CT images calculated by the position calculating unit 46a. Further, the position estimating unit 46c estimates the couchtop positions revised by the position revising unit 46b in the PET images. Accordingly, the PET-CT apparatus according to the first embodiment is able to estimate the couchtop positions in the PET images more accurately.

Furthermore, according to the first embodiment, the controlling unit 48 exercises control so that the PET images on which the position aligning process has been performed by the correction processing unit 46d are displayed after being combined with the X-ray CT images. Consequently, the PET-CT apparatus according to the first embodiment is able to provide persons who interpret the images with such images that do not cause a sense of incongruity and thus enables an accurate interpretation.

Second Embodiment

In the first embodiment described above, the example is explained in which the positional gaps in the Y-axis direction caused by the couchtop sagging are corrected. In a second embodiment, an example will be explained in which, in addition to the positional gaps in the Y-axis direction, positional gaps in the X-axis direction caused by, for example, a gap between devices that occurs during an installation of the devices are corrected. The X-axis-direction correcting process explained below is related to, for example, the gap between the devices that occurs during an installation of the devices, or the like, as explained above. In other words, because the gap in the X-axis direction is different for each of the devices, the X-axis-direction gap is corrected for each of all the devices. In the second embodiment, the processes performed by the position calculating unit 46a and the correction processing unit 46d are different from those in the first embodiment. Thus, the second embodiment will be explained below while a focus is placed on those processes.

Figure 19:
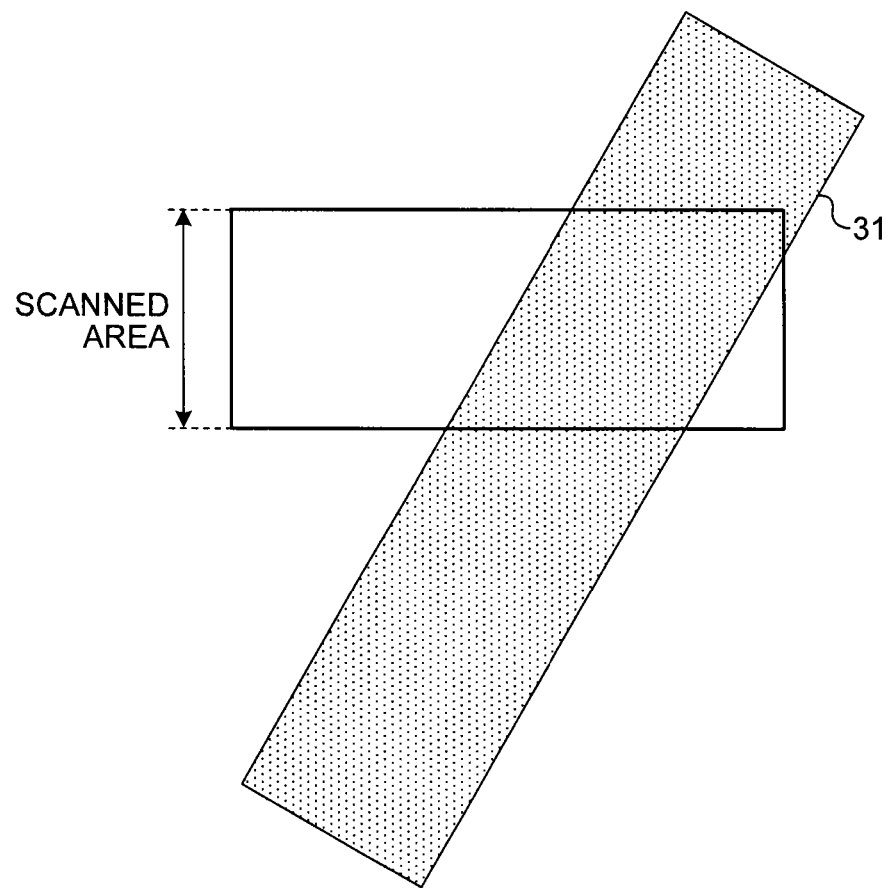
FIG. 19 is a drawing for explaining a gap between devices.

First, the gap between the devices will be explained. FIG. 19 is a drawing for explaining the gap between the devices. FIG. 19 is a top view obtained when the couchtop 31 is inserted into a PET gantry device. An example of a gap between devices can be explained with a situation where, as shown in FIG. 19, the couchtop 31 is inserted, not perpendicularly to the scanned area of the PET gantry device 1, but diagonally at an angle. The couchtop positions in the images taken by using the step-and-shoot method in this situation are shown in FIG. 20.

Figure 20:
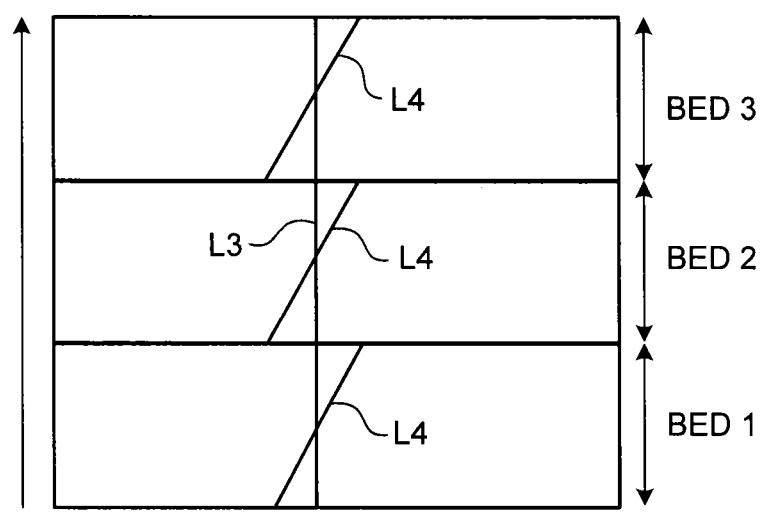
FIG. 20 is a drawing for explaining X-axis-direction positional gaps between images taken by using the step-and-shoot method and images taken by using the helical scanning method.

FIG. 20 is a drawing for explaining X-axis-direction positional gaps between the images taken by using the step-and-shoot method and the images taken by using the helical scanning method. In FIG. 20, coronal planes of the taken images corresponding to the different beds are shown. In other words, cross sections along the body-axis direction of the patient are shown in FIG. 20. Further, in FIG. 20, the couchtop positions (the straight lines L4) in the images taken by using the step-and-shoot method and the couchtop positions (the straight lines L3) in the images taken by using the helical scanning method in FIG. 8 are shown.

When the couchtop 31 is inserted into the scanned area of the PET gantry device 1 diagonally, there are positional gaps of the couchtop between the images taken by using the mutually-different image taking methods because of the difference in the insertion angles, as indicated by the straight lines L3 and L4 in FIG. 20.

To cope with this situation, a PET-CT apparatus according to the second embodiment corrects the positional gaps between the images shown in FIG. 20. More specifically, the PET-CT apparatus according to the second embodiment stores therein, in advance, the couchtop positions in the images taken by using the step-and-shoot method that are obtained by a designer or an operator of the apparatus.

For example, the designer or the operator causes the PET-CT apparatus according to the second embodiment to take X-ray CT images by using the step-and-shoot method and to store therein, in advance, the couchtop positions rendered in the taken X-ray CT images. Further, every time an X-ray CT examination that uses the helical scanning method is performed, the PET-CT apparatus according to the second embodiment reads the stored couchtop positions and corrects the X-axis-direction positional gaps between the images.

To detect the gaps between the couchtop positions in the X-axis direction, the position calculating unit 46a according to the second embodiment uses an area in which it is possible to detect an X-axis-direction movement for each of the slices with respect to the couchtop rendered in the X-ray CT images, as a target area for which the couchtop positions are to be calculated.

FIG. 21 is a drawing that schematically illustrates an exemplary process performed by the position calculating unit 46a according to the second embodiment. In FIG. 21, a cross-sectional image reconstructed from X-ray projection data by the CT image reconstructing unit 42 is shown. For example, as shown in FIG. 21, the position calculating unit 46a first detects an edge 31b of the couchtop 31 rendered in the cross-sectional image and cuts out an area containing the detected edge 31b of the couchtop 31. Further, the position calculating unit 46a calculates an X-axis-direction coordinate of the edge 31b of the couchtop 31 contained in the cut-out area.

The position calculating unit 46a performs the process to detect the edge of the couchtop and the process to calculate the X-axis-direction position of the edge of the couchtop, with respect to each of all the cross-sectional images reconstructed from the X-ray projection data by the CT image reconstructing unit 42. In other words, the position calculating unit 46a performs the process to calculate the X-axis-direction position on the plurality of X-ray CT images taken by using the step-and-shoot method and on the plurality of X-ray CT images taken by using the helical scanning method. Further, the position calculating unit 46a stores the calculated X-axis-direction positions into the correction data 47. The position calculating unit 46a detects the couchtop edge in the images by employing, for example, a method that uses profiles of the images and/or a pattern matching method that uses a template having the shape of the couchtop edge.

The correction processing unit 46d according to the second embodiment corrects the positional gaps in the X-axis direction between the images taken by using the helical scanning method and the images taken by using the step-and-shoot method, based on the couchtop positions calculated by the position calculating unit 46a. More specifically, the correction processing unit 46d reads the X-axis-direction positions of the couchtop edge for the mutually-different image taking methods that are stored in the correction data 47 and corrects the X-axis-direction positional gaps based on the read positions.

Figure 22A:
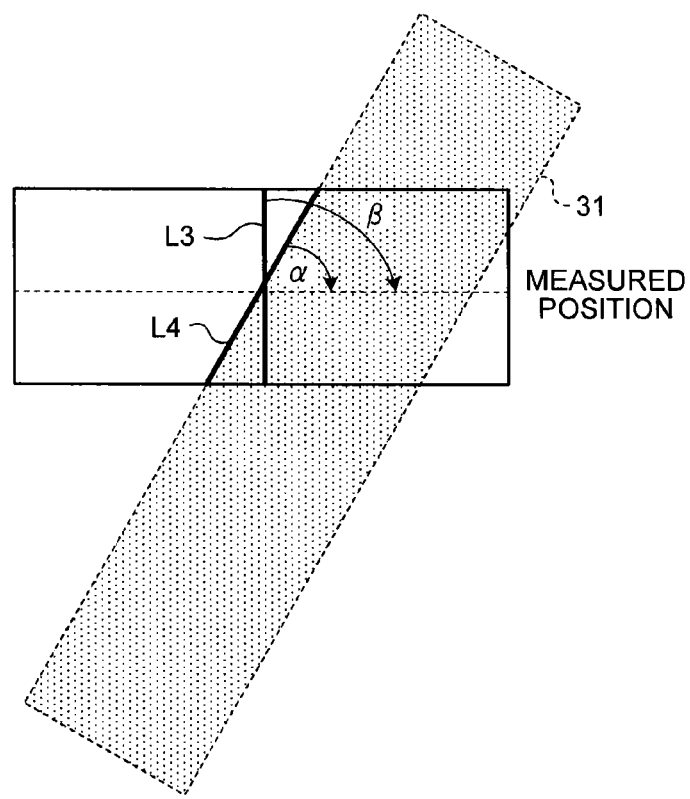
FIG. 22A is a top view of a situation where a couchtop 31 is inserted into a CT gantry device 2.
Figure 22B:
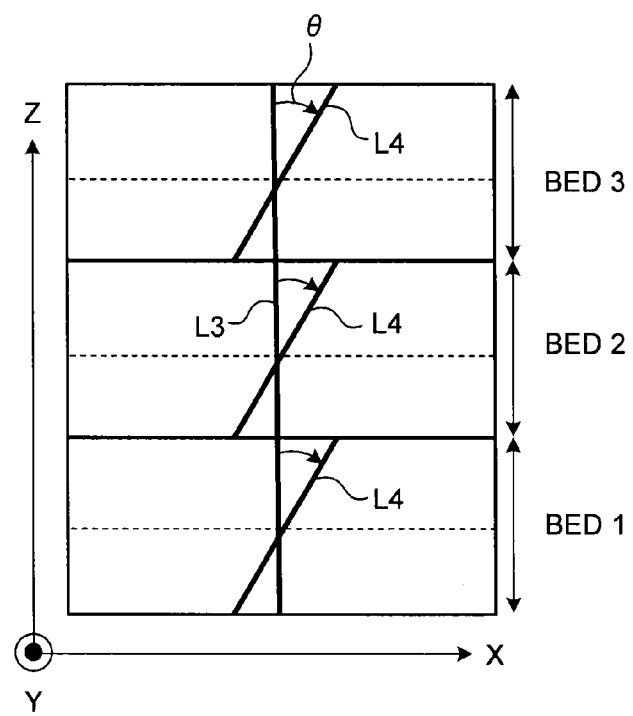
FIG. 22B is a drawing of coronal planes of taken images corresponding to different beds.

Next, an exemplary process performed by the correction processing unit 46d according to the second embodiment will be explained, with reference to FIGS. 22A and 22B. FIG. 22A is a top view of a situation where the couchtop 31 is inserted into the CT gantry device 2. FIG. 22B is a drawing of coronal planes of taken images corresponding to the different beds.

For example, as shown in FIG. 22A, the correction processing unit 46d measures, for each of the beds, an angle "α" between the straight line L4 indicating the position of the couchtop edge in the image taken by using the step-and-shoot method and stored in the correction data 47 and a measured position (a slice plane). Further, as shown in FIG. 22A, the correction processing unit 46d measures, for each of the beds, an angle "β" between the straight line L3 indicating the position of the couchtop edge in the image taken by using the helical scanning method and stored in the correction data 47 and a measured position (a slice plane).

After that, as shown in FIG. 22B, the correction processing unit 46d calculates "θ", which is the difference between the measured angles "α" and "β", for each of the beds. In other words, the correction processing unit 46d calculates "θ" as a value indicating the degree of the positional gap in the X-axis direction. Further, by using Expression (4) shown below, the correction processing unit 46d calculates a correction amount in the X-axis direction for each of the slices. In Expression (4), "X'(slice)" denotes the correction amount in the X-axis direction for each of the slices. Also, in Expression (4), "Z'(slice)" denotes the distance in the Z-axis direction from the slice at the center of the bed.

$$X'(\text{slice}) = Z'(\text{slice}) * \tan(\theta) \quad (4)$$

Figure 23A:
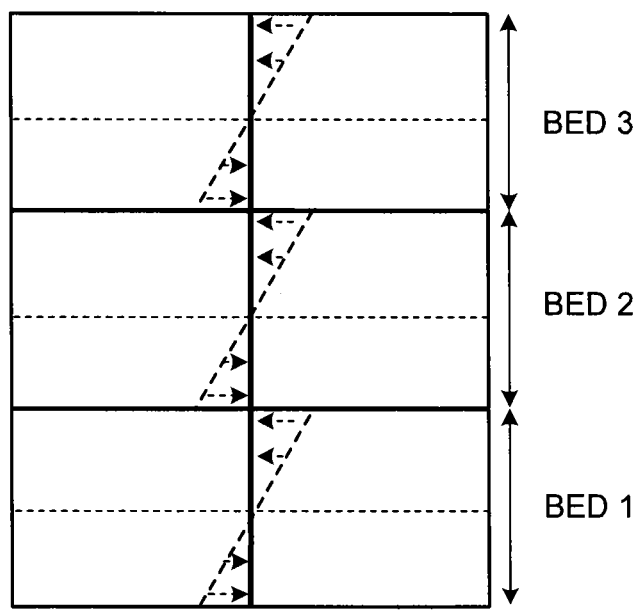
FIG. 23A is a drawing that schematically illustrates a first example of a position aligning process performed by a correction processing unit 46d according to the second embodiment.
Figure 23B:
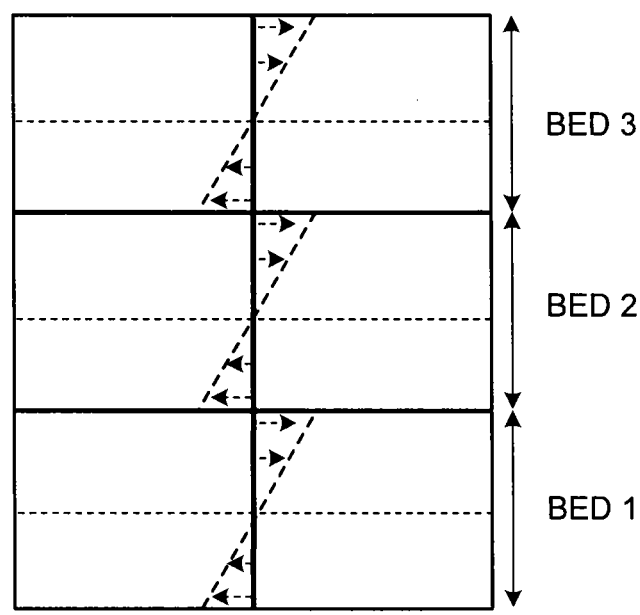
FIG. 23B is a drawing that schematically illustrates a second example of the position aligning process performed by the correction processing unit 46d according to the second embodiment.

In other words, as shown in Expression (4), the correction processing unit 46d calculates the correction amount in the X-axis direction for each of the slices, by multiplying the distance from the center of the bed by the positional gap angle. Further, the correction processing unit 46d corrects the positional gap in the X-axis direction, based on the calculated correction amount for each of the slices. FIG. 23A is a drawing that schematically illustrates a first example of a position aligning process performed by the correction processing unit 46d according to the second embodiment. FIG. 23B is a drawing that schematically illustrates a second example of the position aligning process performed by the correction processing unit 46d according to the second embodiment. In FIGS. 23A and 23B, coronal planes of the taken images corresponding to different beds are shown.

For example, as shown in FIG. 23A, the correction processing unit 46d performs an X-axis-direction correcting process so as to cause the PET image taken by using the step-and-shoot method to match the X-ray CT image taken by using the helical scanning method, for each of beds 1, 2, and 3. Further, as shown in FIG. 23B, the correction processing unit 46d performs an X-axis-direction correcting process so as to cause the X-ray CT image taken by using the helical scanning method to match the PET image taken by using the step-and-shoot method, for each of beds 1, 2, and 3.

Next, the X-axis-direction correcting process performed by the PET-CT apparatus according to the second embodiment will be explained, with reference to FIG. 24. The process shown in FIG. 24 corresponds to the process at step S102 shown in FIG. 16. The image processing procedure performed by the PET-CT apparatus according to the second embodiment is the same as the image processing procedure performed by the PET-CT apparatus according to the first embodiment. Thus, the explanation thereof will be omitted.

Figure 24:
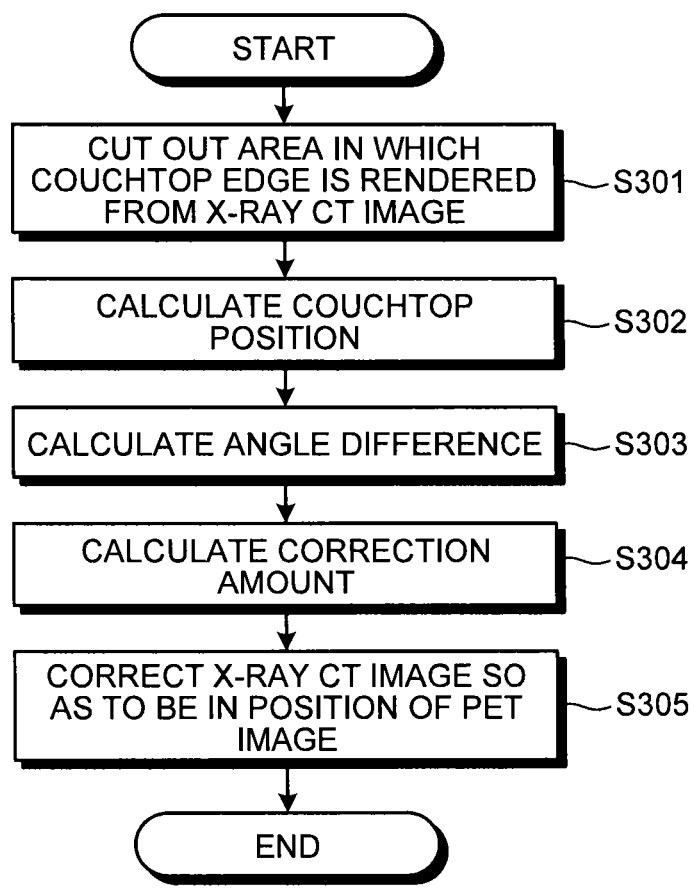
FIG. 24 is a flowchart of an X-axis-direction correcting process performed by a PET-CT apparatus according to the second embodiment.

FIG. 24 is a flowchart of the X-axis-direction correcting process performed by the PET-CT apparatus according to the second embodiment. Shown in FIG. 24 is a process that is performed after the couchtop positions are calculated by using the X-ray CT images taken by using the step-and-shoot method, and subsequently an X-ray CT examination that uses the helical scanning method and a PET examination that uses the step-and-shoot method are performed on a patient.

As shown in FIG. 24, in the PET-CT apparatus according to the second embodiment, the position calculating unit 46*a* cuts out an area in which the edge of the couchtop is rendered in the X-ray CT image (step S301), and calculates the couchtop position (step S302).

Subsequently, the correction processing unit 46*d* calculates the difference between the angles by using the couchtop position in the image taken by using the step-and-shoot method and stored in the correction data 47 and the couchtop position in the X-ray CT image calculated by the position calculating unit 46*a* (step S303).

Further, the correction processing unit 46*d* calculates a correction amount by using the calculated angle and the distance from the slice at the center of the bed (step S304). After that, the correction processing unit 46*d* corrects the X-ray CT image so as to be in the position of the PET image, based on the calculated correction amount (step S305), and the process is thus ended. The correcting process to align the PET image with the position of the X-ray CT image is performed in a similar manner as the Y-axis-direction correcting process performed at step S105 in FIG. 16.

As explained above, according to the second embodiment, the position calculating unit 46*a* calculates the positions of the couchtop in the X-axis-direction. Accordingly, the PET-CT apparatus according to the second embodiment is able to correct the positional gaps caused by the gaps between the devices that occur, for example, during an installation of the devices, with respect to the images taken by using the helical scanning method and the image taken by using the step-and-shoot method and thus makes it possible to inhibit the deterioration of the precision level of the images caused by the positional gaps between the images taken by using the mutually-different image taking methods.

Third Embodiment

Although the first and the second embodiment is explained above, it is possible to implement the disclosed features in various different forms other than those described in the first embodiment.

(1) Modalities

In the first and the second embodiments described above, the examples are explained where the PET-CT apparatus is used as an apparatus in which medical image diagnosis apparatuses using mutually-different image taking methods are integrated together; however, the disclosed features are not limited to those examples. For instance, it is acceptable to use other apparatuses such as a SPECT-CT apparatus. In other words, it is acceptable to use any other apparatus as long as the apparatus has integrated therein a modality for taking images by using the helical scanning method and a modality for taking images by using the step-and-shoot method.

(2) Calculating the Correction Amounts

In the first and the second embodiments described above, the examples are explained in which the correction amounts are calculated every time an X-ray CT examination and a PET examination are performed; however, the disclosed features are not limited to those examples. For instance, another arrangement is acceptable in which the correction amounts are calculated in advance so that the PET-CT apparatus stores the calculated correction amounts therein. In that situation, when a medical examination is performed, the PET-CT apparatus performs the process to correct the positional gaps between the images by using the stored correction amounts.

(3) Generating the Attenuation Map

In the first and the second embodiments described above, the examples are explained in which the attenuation map is generated after the position aligning process is performed on the X-ray CT images; however, the disclosed features are not limited to those examples. For instance, another arrangement is acceptable in which, after an attenuation map is generated from X-ray CT images, a position aligning process is performed on the generated attenuation map.

(4) Targets of the Position Aligning Process

In the first and the second embodiments described above, the examples are explained in which the position aligning process is performed by using the positions of the couchtop rendered in the X-ray CT images; however, the disclosed features are not limited to those examples. For instance, it is also acceptable to perform the position aligning process by using the position of a wire that is used during treatment planning or the like.

(5) Calculating the Couchtop Positions

In the first and the second embodiments described above, the examples are explained in which the couchtop position is calculated after the couchtop area rendered in the X-ray CT image is cut out; however, the disclosed features are not limited to those examples. For instance, it is also acceptable to use the reconstructed X-ray CT image itself.

(6) Image Taking Methods

In the first and the second embodiments described above, the examples are explained in which the X-ray CT images are taken by using the helical scanning method; however, the disclosed features are not limited to those examples. For instance, it is acceptable to take the X-ray CT images by using the step-and-shoot method. Examples of an X-ray CT apparatus that takes X-ray CT images by using the step-and-shoot method include an area detector CT apparatus including an area detector.

Figure 25:
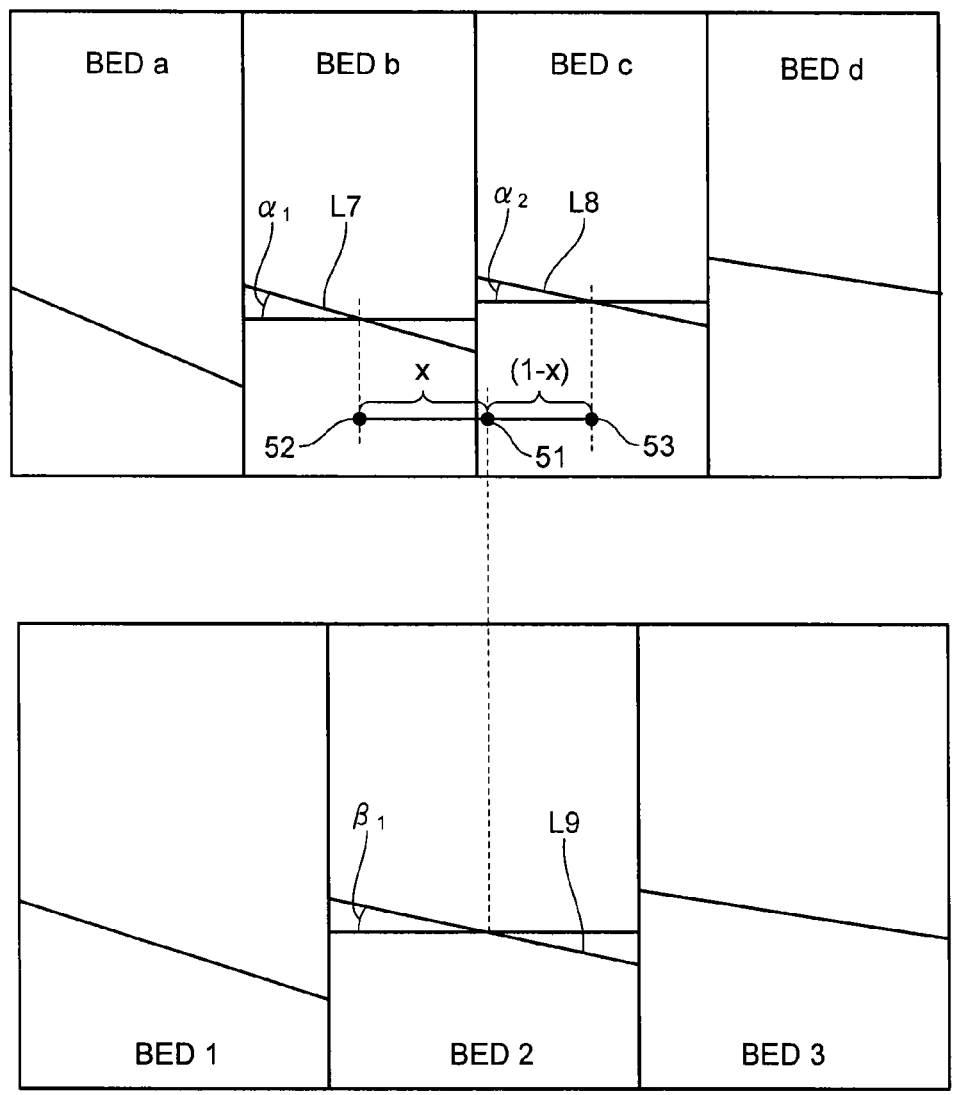
FIG. 25 is a drawing that schematically illustrates an exemplary process performed by a position estimating unit 46c according to a third embodiment.

The area detector CT apparatus includes, for example, a 320-row area detector configured to detect 320 rows at the same time by using a slice width of 0.5 millimeters and performs a scanning process for a width of 160 millimeters each time. FIG. 25 is a drawing that schematically illustrates an exemplary process performed by the position estimating unit 46*c* according to a third embodiment. Shown in FIG. 25 are sagittal planes of X-ray CT images (the top part of FIG. 25) taken by using the step-and-shoot method and sagittal planes of PET images (the bottom part of FIG. 25) taken by using the step-and-shoot method. In FIG. 25, beds a, b, c, and d denote the image taking positions for the X-ray CT images taken by using the step-and-shoot method. Further, in FIG. 25, beds 1, 2, and 3 denote the image taking positions for the PET images taken by using the step-and-shoot method.

Because the width of the detector in the PET device is larger than the width (e.g., 160 millimeters) of the area detector in the X-ray CT device, the width of each of beds 1, 2, and 3 is larger than the width of each of beds a, b, c, and d, as shown in FIG. 25. In this situation, the position estimating unit 46c according to the third embodiment first extracts beds in the X-ray CT device corresponding to a bed in the PET image. For example, as shown in FIG. 25, the position estimating unit 46c extracts beds b and c as the beds in the X-ray CT device corresponding to bed 2 in the PET image.

Further, the position estimating unit 46c identifies the position of the slice at the center of the bed in the PET image corresponding to the extracted beds in the X-ray CT device. For example, as shown in FIG. 25, the position estimating unit 46c identifies a position 51 of the slice at the center of bed 2 corresponding to the extracted beds b and c. Further, the position estimating unit 46c calculates a ratio between the distances from the identified position to the slices at the center of the beds. For example, as shown in FIG. 25, the position estimating unit 46c calculates the ratio "x:(1-x)" between the distance from the position 51 to a position 52 and the distance from the position 51 to a position 53, while the distance from the position 52 of the slice at the center of bed b and the position 53 of the slice at the center of bed c is expressed as "1".

Further, the position estimating unit 46c calculates the gradient of the couchtop in the PET image by using the calculated ratio between the distances and the gradients of the couchtop of the extracted beds of the X-ray CT device. For example, the position estimating unit 46c calculates, for each of the beds, the gradient of the couchtop in the PET image, by using Expression (5) below. In Expression (5), "$\beta_1$" denotes the angle of the couchtop of bed 2. Further, "$\alpha_1$" in Expression (5) denotes the angle of the couchtop L7 of bed b, whereas "$\alpha_2$" in Expression (5) denotes the angle of the couchtop L8 of bed c.

$$\beta_1 = \alpha_1 \times (1-x) + \alpha_2 \times x \quad (5)$$

In other words, the position estimating unit 46c multiplies the angle "$\alpha_1$" of the couchtop of each of the beds in the X-ray CT image corresponding to the bed in the PET image by the ratio between the distances "(1-x)" and multiplies the angle "$\alpha_2$" of the couchtop by the ratio between the distances "x". Further, the position estimating unit 46c calculates the sum of the results of the multiplications as the angle (the gradient) "$\beta_1$" of the couchtop in the PET image.

After that, the position estimating unit 46c determines a straight line L9 going through the slice at the center at the calculated angle, to be the couchtop position of bed 2. The position estimating unit 46c estimates the couchtop position for each of the beds, by performing the process described above for each of the beds in the PET image. If three or more beds of the X-ray CT device correspond to a bed in the PET image, the position estimating unit 46c extracts two beds, i.e., the bed containing the position of the slice at the center of the bed in the PET image and the bed positioned adjacent thereto.

As explained above, the image diagnosis apparatuses according to the first to the third embodiment are configured so as to estimate the couchtop position for each of the beds (the image taking positions) in the PET image, based on the center of the bed and the couchtop position in the X-ray CT image in the vicinity. Further, the image diagnosis apparatuses according to the first to the third embodiment are configured so as to perform the position correcting process on the PET images and the X-ray CT images by using the estimated couchtop positions. The exemplary embodiments described above are only examples, and the scope of the invention is not limited to these examples.

As explained above, according to the first to the third embodiments, it is possible to inhibit the deterioration of the precision level of the images caused by the positional gaps between the images taken by using the mutually-different image taking methods.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image diagnosis apparatus comprising:
    a first image taking device configured to take an image of a patient placed on a couchtop by using an X-ray emission;
    a second image taking device configured to take images in positions by moving an image taking position of the patient by a predetermined distance at a time, along a body-axis direction; and
    processing circuitry configured to
        estimate a couchtop position for each of the image taking positions of the second image taking device, based on information about warping of the couchtop in a plurality of images taken by the first image taking device,
        use information about the couchtop positions estimated for performing a position correcting process on the images obtained by the image taking devices,
        reconstruct the images taken by the second image taking device by using an attenuation map based on the images that have been taken by the first image taking device and have been corrected, and
        correct positional gaps of the reconstructed images with respect to the images that have been taken by the first image taking device.

2. The image diagnosis apparatus according to claim 1, wherein the first image taking device performs a helical scanning process on the patient placed on the couchtop.

3. The image diagnosis apparatus according to claim 1, wherein
    the first image taking device takes images in positions by moving an image taking position of the patient by a predetermined distance at a time, along the body-axis direction, and
    the second image taking device takes the images in the positions by moving the image taking position of the patient by a distance longer than the distance used by the first image taking device, along the body-axis direction.

4. The image diagnosis apparatus according to claims 1, wherein the processing circuitry is configured to
    calculate, as the information about the warping of the couchtop, a position of a structure that exhibits a behavior identical to that of the couchtop rendered in each of a plurality of first images taken by the first image taking device and estimate a couchtop position in a second image taken by the second image taking device by using the calculated position of the structure, and use the couchtop position in the second image that is estimated for performing a position correcting process on the first image and the second image that are obtained by taking images of a substantially same position of the patient.

5. The image diagnosis apparatus according to claim 4, wherein the processing circuitry is configured to calculate a position in a vertical direction from a top surface of the couchtop, as the position of the structure.

6. The image diagnosis apparatus according to claim 4, wherein the processing circuitry is configured to calculate a position in a horizontal direction from a top surface of the couchtop, as the position of the structure.

7. The image diagnosis apparatus according to claim 4, wherein the processing circuitry is further configured to
revise the position of the structure in each of the plurality of first images, based on the position of the structure in each of the plurality of first images calculated, and
estimate the couchtop position in the second image by using the positions of the structure revised.

8. The image diagnosis apparatus according to claim 4, wherein the processing circuitry is further configured to exercise control so that one of the first and the second images on which the position correcting process has been performed is combined with one of the second and the first images before the position correcting process is performed thereon and so that a combined image is displayed by a predetermined display.

9. A method comprising:
an estimating step of estimating a couchtop position for each of image taking positions of a second image taking device configured to take images in positions by moving an image taking position of a patient by a predetermined distance at a time, along a body-axis direction, based on information about warping of a couchtop in a plurality of images taken by a first image taking device configured to take an image of the patient placed on the couchtop by using an X-ray emission;
a position correcting step of using information about the couchtop positions estimated at the estimating step, for performing a position correcting process on the images obtained by the image taking devices;
a reconstructing step of reconstructing the images taken by the second image taking device by using an attenuation map based on the images that have been taken by the first image taking device and have been corrected; and
a correcting step of correcting positional gaps of the reconstructed images with respect to the images that have been taken by the first image taking device.

10. The image diagnosis apparatus according to claim 1, wherein
the first image taking device is an X-ray computed tomography apparatus, and
the second image taking device is a PET (Positron Emission Tomography) apparatus.

11. The image diagnosis apparatus according to claim 1, wherein
the first image taking device is an X-ray computed tomography apparatus, and
the second image taking device is a SPECT (Single Photon Emission Computed Tomography) apparatus.

12. The image diagnosis apparatus according to claim 1, wherein the processing circuitry is configured to obtain the information about warping of the couchtop based on axial images.

13. The image diagnosis apparatus according to claim 1, wherein the processing circuitry is configured to, for each image taking positions, calculate a gradient of the couchtop in a plurality of second images taken by the second image taking device based on the information about warping of the couchtop and information about initial gradient of the couchtop without any weight applied, and estimate, as the couchtop position in the plurality of second images, a plurality of positions changed so that each of couchtop position in a plurality of first images taken by the first image taking device is equal to the gradient calculated without changing a position in the image at center of the image taking position.

14. The image diagnosis apparatus according to claim 1, wherein the processing circuitry is configured to
correct a plurality of first images taken by the first image taking device so as to be in the positions of a plurality of second images taken by the second image taking device, respectively,
generate the attenuation map by using the plurality of first images on which the position correcting process has been performed, and
reconstruct the plurality of second images by using the attenuation map.

* * * * *

UNITED STATES PATENT AND TRADEMARK OFFICE
CERTIFICATE OF CORRECTION

PATENT NO. : 9,433,388 B2
APPLICATION NO. : 13/891786
DATED : September 6, 2016
INVENTOR(S) : Yasuhiro Noshi et al.

Page 1 of 1

It is certified that error appears in the above-identified patent and that said Letters Patent is hereby corrected as shown below:

On the Title Page

Item (71), the Applicant's Information is incorrect. Item (71) should read:
-- (71) Applicant: Toshiba Medical Systems Corporation, Otawara-shi (JP) --

Item (73), the Assignee's Name is incorrect. Item (73) should read:
-- (73) Assignee: Toshiba Medical Systems Corporation, Otawara-shi (JP) --

Signed and Sealed this
Sixth Day of March, 2018

Andrei Iancu
*Director of the United States Patent and Trademark Office*